US012605411B2

(12) United States Patent
Beadnall et al.

(10) Patent No.: US 12,605,411 B2
(45) **Date of Patent: *Apr. 21, 2026**

(54) PHOSPHOLIPID COMPOSITIONS FOR DELIVERY OF THERAPEUTIC COMPOUNDS

(71) Applicant: Aker BioMarine Human Ingredients AS, Lysaker (NO)

(72) Inventors: Thomas Beadnall, Lysaker (NO); Finn Myhren, Lysaker (NO); Nils Hoem, Lysaker (NO)

(73) Assignee: Aker BioMarine Human Ingredients AS, Lysaker (NO)

( * ) Notice: Subject to any disclaimer, the term of this patent is extended or adjusted under 35 U.S.C. 154(b) by 14 days.

This patent is subject to a terminal disclaimer.

(21) Appl. No.: 18/734,385

(22) Filed: Jun. 5, 2024

(65) Prior Publication Data

US 2025/0057891 A1 Feb. 20, 2025

Related U.S. Application Data

(63) Continuation of application No. 18/381,439, filed on Oct. 18, 2023, now Pat. No. 12,023,359.

(30) Foreign Application Priority Data

Nov. 1, 2022 (NO) .................................... 20221173

(51) Int. Cl.
*A61K 9/107* (2006.01)
*A61K 31/202* (2006.01)
*A61K 35/612* (2015.01)

(52) U.S. Cl.
CPC ............ *A61K 35/612* (2013.01); *A61K 9/107* (2013.01); *A61K 31/202* (2013.01)

(58) Field of Classification Search
CPC ...................................................... A61K 9/107
See application file for complete search history.

(56) References Cited

U.S. PATENT DOCUMENTS

| | | | |
|---|---|---|---|
| 2008/0044487 A1 | 2/2008 | Bruheim |
| 2016/0175366 A1 | 6/2016 | Hupfeld |

FOREIGN PATENT DOCUMENTS

| | | |
|---|---|---|
| DK | 17196964 | 3/2020 |
| WO | WO 03/011873 | 2/2003 |
| WO | WO 2008/117062 | 10/2008 |
| WO | WO 2011/051743 | 5/2011 |
| WO | WO 2013/033618 | 3/2013 |
| WO | WO 2016/128838 | 2/2016 |
| WO | WO 2018/061007 | 4/2018 |
| WO | WO 2019/123015 | 6/2019 |
| WO | WO 2020/044118 | 3/2020 |
| WO | WO 2020/254675 | 6/2020 |
| WO | WO 2021/022378 | 2/2021 |
| WO | WO 2021/202680 | 3/2021 |

OTHER PUBLICATIONS

Norwegian Search Report, NO Patent Application No. 20221173, dated Mar. 14, 2023, 3 pages.

Zhao et al. Preparation and Characterization of Microemulsions Based on Antarctic Krill Oil, Marine Drugs, 2020, vol. 18, issue 10, Nr. 492, 21 pages.

Velasco-Rodriguez et al. Krill Lecithin as Surfactant for Preparation of Oil/Water Nanoemulsions as Curcumin Carriers, Eur. J. Lipid Sci. Technol. Sep. 2021, vol. 123, issue 9, nr 200238, 23 pages.

International Patent Application No. PCT/IB2023/056584, filed Jun. 26, 2023, 76 pages.

Raatz S K et al: "Enhanced Absorption of n-3 Fatty Acids from Emulsified Compared with Encapsulated Fish Oil", Journal of the American Dietetic Association, The Association, Chicago, IL, US, vol. 109, No. 6, Jun. 1, 2009, pp. 1076-1081.

International Search Report and Written Opinion, Application No. PCT/IB2023/060534, dated Feb. 13, 2024, 15 pages.

Heras et al. The potential use of lipid microspheres as nutritional supplements for adult Ostrea edulis. Aquaculture (1994), vol. 123, No. 3/4, pp. 309-322.

*Primary Examiner* — Qiuwen Mi
(74) *Attorney, Agent, or Firm* — Casimir Jones, S.C.; J. Mitchell Jones

(57) ABSTRACT

The present invention relates to compositions comprising phospholipids for delivery of bioactive compounds such as ethyl esters, fish oil concentrates, cannabinoids, CoQ10 and curcumin under conditions such the bioavailability of the bioactive compounds is enhanced.

16 Claims, 10 Drawing Sheets

PHOSPHOLIPID COMPOSITIONS FOR DELIVERY OF THERAPEUTIC COMPOUNDS

CROSS-REFERENCE TO RELATED APPLICATION

The present application is a continuation of U.S. patent application Ser. No. 18/381,439 filed Oct. 18, 2023, which claims priority to Norwegian application Ser. No. 20221173, filed Nov. 1, 2022, the contents of which are herein incorporated by reference in their entireties for all purposes.

FIELD OF THE INVENTION

The present invention relates to compositions with that provide increased bioavailability of therapeutic compounds, and in particular to compositions that comprise phospholipids for delivery of therapeutic lipophilic compounds.

BACKGROUND OF THE INVENTION

Bioactive substances, intended to promote good health, must be absorbed in the intestine and enter the systemic circulation in order to achieve the desired effects. Bioavailability, or the extent a substance is absorbed and becomes available to the site of action, is dependent on multiple factors, including aqueous solubility, permeability, dissolution rate, and metabolism [1]. The absorption of a given compound depends largely on the solubility of the substance in the gastrointestinal lumen and the permeability across the intestinal epithelium [2]. The Biopharmaceutical classification system (BCS) is widely used by regulatory bodies to classify substances based on their solubility and intestinal permeability. Low solubility and/or permeability leads to only a small fraction of the substance reaching the systemic circulation and then the site of action, resulting in poor bioavailability and limited health effect [3]. Substances belonging to BCS Class 2 (low solubility), Class 3 (low permeability) and Class 4 (both low solubility and permeability) can benefit from formulations enhancing their bioavailability.

Different solutions to address the problem of poor absorption of lipid-based formulations and lipophilic drugs have been suggested, examples being Advanced Lipid Technologies (ALT) and AquaCelle (Pharmako), a self-micro-emulsifying delivery system (SMEDS), Vesisorb and Lipoid (soyabean lecithin).

Little work has been done to explore the ability of marine phospholipids to act as excipients to aid absorption of substances with low solubility and/or low permeability. Thus, there is still a need in the art for alternative solutions to the problem of enhancing absorption of substances having low solubility and low permeability.

SUMMARY OF THE INVENTION

The present invention provides improved mixes of marine phospholipids and therapeutic ingredients with low solubility and/or low permeability selected from the group of lipophilic substances and substances classified as class 2, 3 or 4 according to the Biopharmaceutical classification system (BCS), included, but not limited to, omega-3 ethyl esters (e.g., Lovaza, Epanova, Vacepa) omega-3 triglycerides, CBD, curcumin, CoQ10, fisetin and quercetin.

As demonstrated by Example 1, the inventors have found improved mixes with the proper level of marine phospholipid necessary to provide stable emulsions with emulsion droplet size that are known to be readily absorbed in the stomach, thereby enhancing absorption of additional omega-3 fatty acids. Ex 1 further demonstrates the optimal ratio between mixes with marine phospholipids and omega-3 fish oil concentrates (ethyl esters and triglyceride) to provide emulsions with the smallest droplet size. Smaller droplet sizes will provide a higher surface area which allows for more rapid digestion into omega 3 free fatty acids readily available for absorption.

Example 2 provides in vitro demonstration that enhanced bioavailability of curcumin, a BCS class 4 substance, can be achieved when formulated in a composition with marine phospholipids. The absorption characteristics of curcumin can be even more improved in combination with krill PLs (>40% w/w) with processing techniques to improve the solubility of curcumin further.

Example 4 provides a small clinical study demonstrating significant absorption from baseline of CoQ10, a BCS class 2 substance, formulated with krill phospholipids (>40% w/w). No significant absorption was observed in the group with a comparator CoQ10-product.

In some preferred embodiments, the present invention provides a lipid formulation for use in therapy by enhancing absorption of a therapeutic ingredient in a subject in need thereof, comprising a) phospholipids from a marine source, wherein the phospholipids comprise more than 80% w/w phosphatidylcholine and wherein the molar content of omega-3 moieties in the phospholipids is more than 25%, and b) a therapeutic ingredient selected from the group of substances classified as class 2, 3 or 4 according to the Biopharmaceutical classification system (BCS) and lipophilic substances from a source different from the marine source of the phospholipids, wherein the lipid formulation comprises more than 17% w/w of phospholipids and forms emulsions with a droplet size of less than 500 nm in an artificial stomach fluid determined through dynamic light scattering, or wherein the lipid formulation comprises more than 17% w/w of phospholipids and forms emulsions selected from the group consisting of emulsions with a droplet size of from 150 nm to 600 nm in an artificial stomach fluid determined through dynamic light scattering, emulsions with an average droplet size of from 150 nm to 600 nm in an artificial stomach fluid, preferably determined through dynamic light scattering, and emulsions wherein at least 80% of the droplets have a droplet size of from 150 nm to 600 nm in an artificial stomach fluid.

In other preferred embodiments, the present invention provides a lipid formulation for use in therapy by enhancing absorption of ethyl esters in a subject in need thereof, comprising:

a) from 17% w/w to 75% w/w total phospholipids, wherein w/w is the weight of the phospholipids per the total weight of the formulation, and wherein the phospholipids comprise more than 80% w/w phosphatidylcholine and wherein the molar content of omega-3 moieties in the phospholipids is more than 25%; and b) from 16% w/w to 50% w/w of ethyl esters of DHA and/or EPA;

wherein the lipid formulation forms an emulsion with a droplet size of from 150 to 600 nm in an artificial stomach fluid determined through dynamic light scattering.

In other preferred embodiments, the invention provides a method for enhancing absorption of a substance in a subject in need thereof comprising administering to the subject a lipid formulation comprising a mix of 1) phospholipid molecules from a marine source, the phospholipid molecules comprising greater than 80% phosphatidylcholine and having more than 25% omega-3 moieties attached to the phospholipid molecules on a molar basis, and 2) a substance selected from the group of lipophilic substances and substances classified as class 2, 3 and 4 according to the Biopharmaceutical classification system (BCS) and wherein the lipid formulation comprises at least 17% w/w of phospholipid molecules and forms emulsions with a droplet size of less than 500 nm in an artificial stomach fluid.

In some preferred embodiments, the present invention provides an emulsifying lipid formulation comprising a mix of phospholipid molecules from a marine source, said phospholipid molecules comprising greater than 80% total phosphatidylcholine and having more than 25% omega-3 moieties attached to said phospholipid molecules on a molar basis, and a substance selected from the group of lipophilic substances and substances classified as BCS class 2, 3 and 4, wherein the substance is from a source different than the marine source selected from the group of ethyl esters, triglycerides, curcumin, coenzyme Q10, CBD, fisetin and quercetin, wherein the lipid formulation comprises at least 17% w/w of phospholipid molecules and forms emulsions with a droplet size of less than 600 nm or 500 nm in an artificial stomach fluid.

In some preferred embodiments, the lipid formulation comprises from 2.5% to 50% w/w of the substance selected from the group of lipophilic substances and substances classified as BCS class 2, 3 and 4 from a source different than the marine source of the phospholipid molecules. In some preferred embodiments, the lipid formulation comprises from 2.5% to 20% w/w of the substance selected from the group of substances classified as BCS class 2, 3 and 4 from a source different than the marine source of the phospholipid molecules. In some preferred embodiments, the lipid formulation comprises from 15% to 50% w/w of the substance selected from the group of substances classified as BCS class 2, 3 and 4 from a source different than the marine source of the phospholipid molecules. In some preferred embodiments, the lipid formulation comprises from 15% to 40% w/w of the substance selected from the group of BCS class 2, 3 and 4 from a source different than the marine source of the phospholipid molecules.

In some preferred embodiments, the substance is a lipophilic substance from a source different than the marine source of the phospholipid molecules selected from the group consisting of ethyl esters, triglycerides and combinations thereof.

In some preferred embodiments, the lipophilic substance from a source different than the marine source of the phospholipid molecules is an ethyl ester selected from the group consisting of ethyl esters of eicosapentaenoic acid and docosahexaenoic acid and combinations thereof. In some preferred embodiments, the lipid formulation comprises from 20% to 50% w/w of the ethyl esters of selected from the group consisting of eicosapentaenoic acid and docosahexaenoic acid and combinations thereof. In some preferred embodiments, the lipid formulation comprises from 25% to 35% w/w of the ethyl esters selected from the group consisting of eicosapentaenoic acid and docosahexaenoic acid and combinations thereof. In some preferred embodiments, the lipid formulation comprises from 27% to 33% w/w of the ethyl esters selected from the group consisting of eicosapentaenoic acid and docosahexaenoic acid and combinations thereof. In some preferred embodiments, the lipid formulation comprises from 28% to 32% w/w of the ethyl esters selected from the group consisting of eicosapentaenoic acid and docosahexaenoic acid and combinations thereof. In some preferred embodiments, the lipid formulation comprises from 29% to 31% w/w of the ethyl esters selected from the group consisting of eicosapentaenoic acid and docosahexaenoic acid and combinations thereof.

In some preferred embodiments, the lipophilic substance from a source different than the marine source of the phospholipid molecules is a fish oil concentrate. In some preferred embodiments, the lipid formulation comprises from 20% to 50% w/w of the fish oil concentrate.

In some preferred embodiments, the substance belonging to BCS class 2, 3 or 4 is selected from the group consisting of a cannabidiol (CBD) compound, a CoQ10 compound, a curcumin compound, and a flavonoid compound, including fisetin and quercetin.

In some preferred embodiments, the substance belonging to BCS class 2, 3 and 4 is a CBD compound and the lipid formulation comprises from 2.5% to 7.5% w/w the CBD compound.

In some preferred embodiments, the substance selected from the group of substances classified as BCS class 2, 3 and 4 is a curcumin compound and the lipid formulation comprises from 15% to 25% w/w the curcumin compound. In some preferred embodiments, the curcumin is first solubilized by mixing the curcumin with krill oil and ethanol to form a solution, then evaporating the ethanol from the solution. In some embodiments, the ratio of ethanol to krill utilized for solubilization of the curcumin is from 1:1 to 7:1 krill oil to ethanol. In some preferred embodiments, the ratio of ethanol to krill utilized for solubilization of the curcumin is from 2:1 to 4:1 krill oil to ethanol.

In some preferred embodiments, the substance selected from the group of substances classified as BCS class 2, 3 and 4 is a CoQ10 compound and the lipid formulation comprises from 15% to 25% w/w the CoQ10 compound.

In some preferred embodiments, the lipid formulation comprises from 17% to 70% w/w of the phospholipid molecules from the marine source. In some preferred embodiments, the lipid formulation comprises from 20% to 60% w/w of the phospholipid molecules from the marine source. In some preferred embodiments, the lipid formulation comprises from 30% to 50% w/w of the phospholipid molecules from the marine source. In some preferred embodiments, the lipid formulation comprises from 35% to 45% w/w of the phospholipid molecules from the marine source. In some preferred embodiments, the lipid formulation comprises from 37% to 43% w/w of the phospholipid molecules from the marine source. In some preferred embodiments, the lipid formulation comprises from 38% to 42% w/w of the phospholipid molecules from the marine source. In some preferred embodiments, the lipid formulation comprises from 39% to 41% w/w of the phospholipid molecules from the marine source.

In some preferred embodiments, the marine source is selected from the group consisting of krill, algae, herring and squid.

In some preferred embodiments, the lipid formulation forms a particle size of less than 400 nm in an artificial stomach fluid. In some preferred embodiments, the lipid formulation forms a particle size of less than 300 nm in an artificial stomach fluid.

In some preferred embodiments, the lipid formulation forms a droplet size of from 150 to 500 nm in an artificial stomach fluid determined through dynamic light scattering. In some preferred embodiments, the lipid formulation forms forms a droplet size of from 150 to 400 nm in an artificial stomach fluid determined through dynamic light scattering. In some preferred embodiments, the lipid formulation forms a droplet size of from 150 to 300 nm in an artificial stomach fluid determined through dynamic light scattering. In some preferred embodiments, the lipid formulation forms a droplet size of from 150 to 250 nm in an artificial stomach fluid determined through dynamic light scattering. In some preferred embodiments, the lipid formulation forms a droplet size of from 150 to 200 nm in an artificial stomach fluid determined through dynamic light scattering.

In some preferred embodiments, the lipid formulation forms an average droplet size of from 150 to 500 nm in an artificial stomach fluid, preferably determined through dynamic light scattering. In some preferred embodiments, the lipid formulation forms an average droplet size of from 150 to 400 nm in an artificial stomach fluid, preferably determined through dynamic light scattering. In some preferred embodiments, the lipid formulation forms an average droplet size of from 150 to 300 nm in an artificial stomach fluid, preferably determined through dynamic light scattering. In some preferred embodiments, the lipid formulation forms an average droplet size of from 150 to 250 nm in an artificial stomach fluid, preferably determined through dynamic light scattering. In some preferred embodiments, the lipid formulation forms an average droplet size of from 150 to 200 nm in an artificial stomach fluid, preferably determined through dynamic light scattering.

In some preferred embodiments, the lipid formulation forms an emulsion comprising droplets wherein at least 80% of the droplets have a droplet size of from 150 to 500 nm in an artificial stomach fluid. In some preferred embodiments, the lipid formulation forms an emulsion comprising droplets wherein at least 80% of the droplets have a droplet size of from 150 to 400 nm in an artificial stomach fluid determined through dynamic light scattering. In some preferred embodiments, the lipid formulation forms an emulsion comprising droplets wherein at least 80% of the droplets have a droplet size of from 150 to 300 nm in an artificial stomach fluid determined through dynamic light scattering. In some preferred embodiments, the lipid formulation forms an emulsion comprising droplets wherein at least 80% of the droplets have a droplet size of from 150 to 250 nm in an artificial stomach fluid determined through dynamic light scattering. In some preferred embodiments, the lipid formulation forms an emulsion comprising droplets wherein at least 80% of the droplets have a droplet size of from 150 to 200 nm in an artificial stomach fluid determined through dynamic light scattering.

In some preferred embodiments, the marine source of the phospholipid molecules is further characterized as being an oil comprising a mixture of phospholipid and triglyceride molecules. In some preferred embodiments, the marine source of the phospholipid molecules is a marine oil. In some preferred embodiments, the marine oil comprises a mixture of at least phospholipid and triglyceride molecules. In some particularly preferred embodiments, the marine oil is krill oil. In some preferred embodiments, greater than 60% (on a molar basis) of the omega-3 moieties in the oil are attached to the phospholipid molecules in the marine oil. In some preferred embodiments, greater than 70% (on a molar basis) of the omega-3 moieties in the oil are attached to the phospholipid molecules in the marine oil. In some preferred embodiments, greater than 75% (on a molar basis) of the omega-3 moieties in the oil are attached to the phospholipid molecules in the marine oil. In some preferred embodiments, from 60% to 90% (on a molar basis) of the omega-3 moieties in the oil are attached to the phospholipid molecules in the marine oil. In some preferred embodiments, from 73% to 83% (on a molar basis) of the omega-3 moieties in the oil are attached to the phospholipid molecules in the marine oil.

DEFINITIONS

Figure 1A:
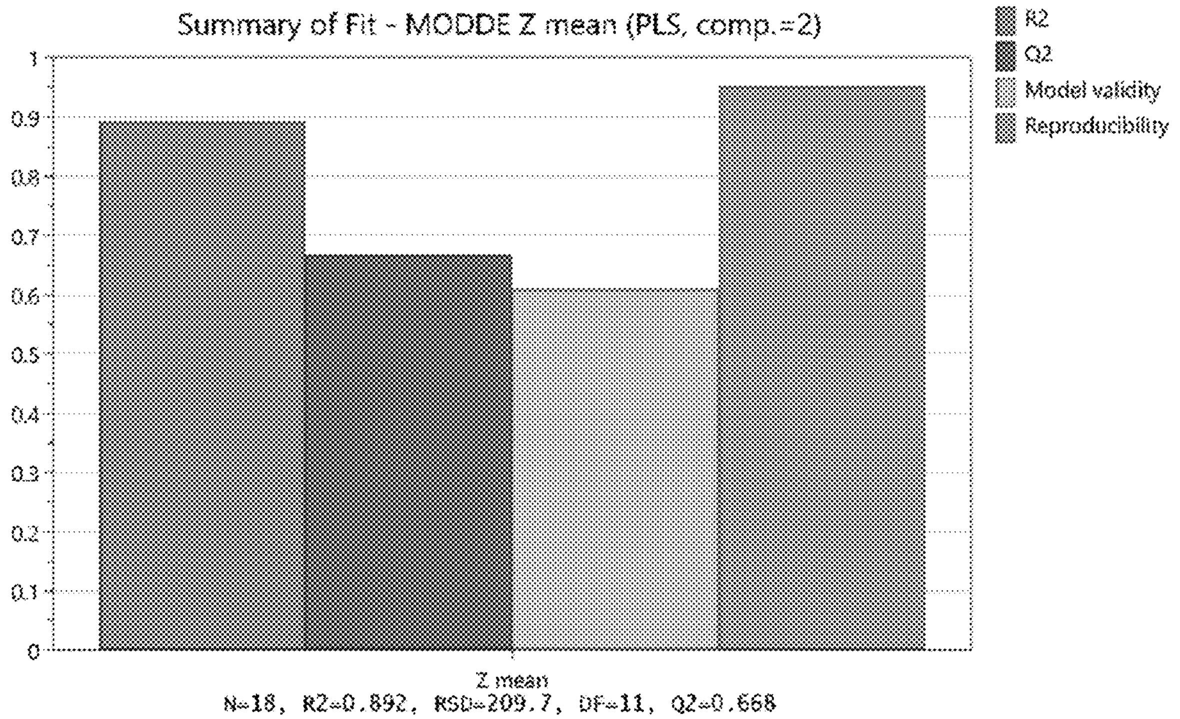
FIGS. 1A-D. Summary of fit (FIG. 1A), coefficients plot (FIG. 1B), observed vs predicted plot (FIG. 1C) and contour plot (FIG. 1D) of the partial least squares (PLS) regression model.

Throughout the present disclosure relevant terms are to be understood consistently with their typical meanings established in the relevant art, i.e. the art of pharmaceutical chemistry, medicine, biology, biochemistry and physiology.

The term “EPA” refers to eicosapentaenoic acid.

The term “DHA” refers to docosahexaenoic acid.

EPA and DHA, as used herein in connection with the compositions of the invention, refers to the fatty acid chain that can be bound to a lipid backbone, such as to phospholipids, lysophospholipids, triacylglycerides, diacylglycerides, monoacylglyceride or any other lipid backbone, or it can exist in the compositions as a free fatty acid or ethyl ester.

The term “total phospholipids” is used herein to describe the total content of phospholipids, including lyso-phospholipids, in a composition. As used herein, “phospholipid” refers to an organic compound that has two fatty acid moieties attached at the sn-1 and sn-2 positions of glycerol, and contains a head group linked by a phosphate residue at the sn-3 position of the glycerol. Exemplary headgroup moieties include choline, ethanolamine, serine and inositol. Phospholipids include phosphatidylcholine, phosphatidylserine, phosphatidylethanolamine, phosphatidylinositol, and phosphatidic acid. The fatty acid moiety is the portion of the fatty acid molecule that is bound at the sn-1 or sn-2 position, for example by an ester or ether linkage. When the fatty acid moiety is a fatty acyl, the aliphatic chain of the fatty acyl is attached via an ester linkage and when the fatty acid moiety is an aliphatic chain of a fatty acid, the aliphatic chain is attached via an ether linkage.

When a particular fatty acid is mentioned in connection with a phospholipid of the invention (e.g., EPA or DHA) it should therefore be taken as a reference to the relevant fatty acyl group or to its aliphatic chain. In krill oil, a predominant amount of the total amount of EPA and/or DHA is bound to a phospholipid, in particular a predominant amount of EPA and/or DHA is bound to phosphatidylcholine.

The term "total phosphatidylcholine" is used herein to describe the total content of phosphatidylcholine, including lyso-phosphatidylcholine (LPC), in a composition.

The term "pharmaceutically acceptable excipients" refer to substances different from the components of the phospholipid-compositions referred to in the claims and which are commonly used with oily pharmaceuticals. Such excipients include, but are not limited to triolein, soybean oil, safflower oil, sunflower oil, sesame oil, castor oil, coconut oil, triglycerides, tributyrin, tricaproin, tricaprylin, vitamin E, antioxidants, α-tocopherol, ascorbic acid, deferoxamine mesylate, thioglycolic acid, emulsifiers, lecithin, polysorbate 80, methylcellulose, gelatin, serum albumin, sorbitan lauraute, sorbitan oleate, sorbitan trioleate, polyethylene glycol (PEG), PEG 400, polyethylene glycol-modified phosphatidylethanolamine (PEG-PE), poloxamers, glycerin, sorbitol, Xylitol, pH adjustment agents; sodium hydroxide, antimicrobial agents EDTA, sodium benzoate, benzyl alcohol and proteins such as albumin. The pharmaceutically acceptable excipients must be acceptable in the sense of being compatible with the other ingredients of the composition and not deleterious to the recipient thereof.

Used herein, the term "pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of pharmaceutical salts properties, Selection, and Use; 2002.

The term "prophylaxis" means measures taken to prevent, rather than treat, diseases or conditions.

The term "therapeutically effective amount" is an art-recognized term. In certain embodiments, the term refers to an amount of the composition disclosed herein that produces some desired effect at a reasonable benefit/risk ratio applicable to the medical treatment. In certain embodiments, the term refers to that amount necessary or sufficient to eliminate, reduce or alleviate medical symptoms for a period of time. The effective amount may vary depending on such factors as the disease or condition being treated, the particular composition being administered, the size of the subject, or the severity of the disease or condition. One of ordinary skill in the art may empirically determine the effective amount of a particular composition without necessitating undue experimentation.

The term "treating" is art-recognized and includes preventing a disease, disorder or condition from occurring in a subject which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes administration of a composition which reduces the frequency of, or delays the onset of, symptoms of a medical condition in a subject relative to a subject which does not receive the composition.

Unless specifically defined herein, all technical and scientific terms used have the same meaning as commonly understood by a skilled artisan in the fields of medicine, pharmacology, pharmaceutical chemistry, biology, biochemistry and physiology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail.

Where a numerical limit or range is stated herein, the endpoints are included. Also, all values and sub ranges within a numerical limit or range are specifically included as if explicitly written out.

Headings have been used for organizational purposes and should not be construed as limiting the subject-matter herein.

DETAILED DESCRIPTION OF THE INVENTION

The present invention relates to compositions comprising marine phospholipids in combination with additional omega-3 fatty acids forms and bioactive components. An advantage with marine phospholipids according to the invention is that the phospholipids exhibit bioactivity due to the incorporation of choline, EPA and DHA. The improved omega-3 formulations of the present invention exhibit increased absorption as well as decreased adverse reaction in users such as decreased burping and reflux. The present invention is not limited to any particular source of marine phospholipids. In some preferred embodiments, the marine phospholipids are derived from a marine source such as krill, fish (e.g., herring), squid, or algae. In some particularly preferred embodiments, the marine phospholipids are krill phospholipids.

Phospholipids are the main component of all our cell membranes, and the phospholipid omega-3 that you receive from krill oil is in the exact form that your body needs for optimal cellular uptake. A phospholipid molecule consists of two fatty acids, which are long chains of carbon and hydrogen molecules. They are attached to a glycerol backbone that is further linked to a phosphate group. The phosphate group has a head group, such as choline, resulting in phosphatidylcholine (PC). Choline, phosphate, and glycerol make up the hydrophilic (water-friendly) side of the molecule, the fatty acid chains are the hydrophobic (water-fearing) part of the molecule.

Phospholipids are amphiphilic in nature, meaning that they have both hydrophilic and hydrophobic parts. This characteristic is important for the structural function of phospholipids, which serve as the building blocks of cell membranes. When phospholipids are exposed to water, the molecules spontaneously arrange such that the tails are shielded from the water, resulting in the formation of membrane structures such as bilayers, vesicles, and micelles.

Phospholipids are multifunctional excipients, thanks to the numerous possible combinations of fatty acids and their diverse associated physiochemical properties [4]. They can form different colloidal structures as they disperse in water, depending on the specific properties or processing conditions (Table 1). Formulation using phospholipids can help enhance the bioavailability of poorly water-soluble therapeutic compounds by increasing their degree of dispersion and solubilization in the GI tract [5, 6] and stimulating the lymphatic transport.

Possible formulations produced with phospholipids can range from simple blends made with a natural phospholipid raw material to sophisticated formulations that may require the use of purified phospholipids and involved processing. Natural phospholipid rich raw material includes krill oil, algae oil, herring roe oil or oil from other marine materials. The feasible type of formulation (could even be multiple choices) must be assessed in each situation. As the krill oil phosphatidylcholine contains mostly long chain, polyunsaturated fatty acids (PUFAs), predominantly EPA and DHA, they provide a more soft and flexible structure that very favorably accommodate additional components in its emulsified stage in the gastric fluids. In this context krill oil phospholipids positively differ from other natural phospholipids (lecithins) from soy and egg that have a higher degree of saturated and more rigid fatty acids, with no presence of EPA and DHA. As demonstrated herein, phospholipids from krill oil can efficiently enhance absorption of such additional components belonging to BCS Class 2 having low solubility and BCS Class 3 having low permeability, particularly lipophilic substances selected from the group of CBD, coenzyme Q10, curcumin, fisetin and quercetin.

TABLE 1

Overview of typical phospholipid formulations, recreated from [2]

| | |
|---|---|
| Phospholipid formulation to improve the oral bioavailability of poorly soluble drugs | Phospholipid-drug complex<br>Liposome<br>Mixed micelle<br>Emulsion<br>Micro-/Nano emulsion<br>Self-emulsifying drug delivery systems (SEDDS)<br>Solid nanoparticles (SLN)<br>Suspension |

Antarctic krill is the most abundant multi-cellular animal species on earth, with one of the largest biomasses of around 500 million metric tons. These small pinkish-red transparent creatures move in huge swarms feeding on microscopic algae, providing them with a diet rich in omega-3s. As a result, krill oil is a pure, natural source of EPA and DHA omega-3 fatty acids. Unlike fish oil whose omega-3s are incorporated into triglycerides, the lipid composition of krill oil is characterized by a high concentration of phospholipids (PLs) carrying EPA and DHA. Omega-3 fatty acids in this form are readily incorporated into tissues in a more effective and efficient manner compared to triglycerides and ethylesters [7]. Therefore, lesser amounts of EPA and DHA can be taken with krill oil compared to fish oil to achieve the same extent of omega-3 health benefits.

Krill oil is a multi-nutrient supplement. In addition to phospholipid-bound omega-3 fatty acids, naturally occurring astaxanthin and choline provide additional health benefits. Astaxanthin contained in krill is a highly potent antioxidant and is the reason for krill oil's red color [8]. It assists in keeping the omega-3 fatty acids in krill oil stable. In the body, astaxanthin provides protection against free radical attack, and normalizes oxidative stress in smoking or overweight individuals. As a result, astaxanthin has been linked with anti-inflammatory and pain-relieving effects, faster recovery from exercise, UV light protection in the skin [9], aging, and health of liver, heart, eye, joint, and prostate [10].

Choline, which makes up about 15% of the phosphatidylcholine (PC) molecule, is also an essential vitamin-like nutrient that is crucial for normal cellular function. Choline and choline derivatives are involved in important biological functions including nerve signaling, cell signaling, and water balance. Therefore, it is not surprising that choline deficiency is associated with fatty liver, cardiovascular diseases, and neurological disorders [11]. Despite its numerous and essential roles in our body, National Health and Nutrition examination Survey in 2003-2004 has surprisingly concluded that 90% of the American population has an inadequate choline intake [12].

Figure 4:
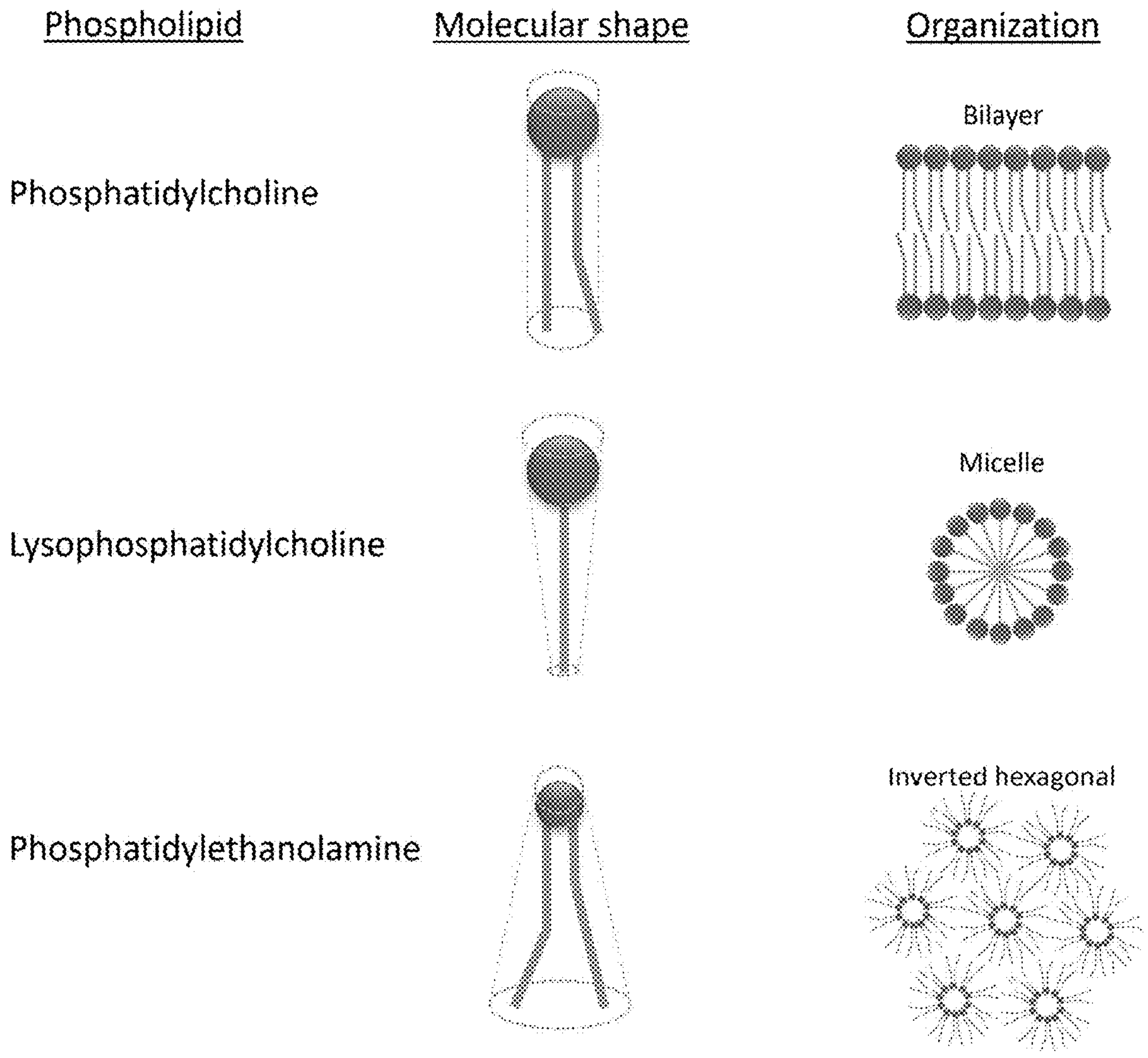
FIG. 4. Effect of lipid polymorphism on formulation. The molecular shape governs how the PLs are organized in an aqueous environment.

In addition to PC, krill oil contains multiple classes of phospholipids, including lysophosphatidylcholine (LPC) and phosphatidylethanolamine (PE), phosphatidylserine (PS) and phosphatidylinositol (PI), and neutral lipids, such as triglycerides, diglycerides, monoglycerides and free fatty acids. When krill oil is properly mixed in an aqueous solution, the water-insoluble neutral lipids are emulsified by the PL to give a homogeneous dispersion. Having a PL composition with a variation in head group and fatty acid composition is thought to be advantageous for making a formulation with more flexible and readily absorbable membrane structures. The fluid mosaic model describes the plasma membrane as a mosaic of components-phospholipids, cholesterol, proteins, and carbohydrates—with the main component being the amphiphilic phospholipid molecules [13]. The combination of this components, as well as polymorphism in the phospholipid molecules, ensure that the membranes possess a fluid character. The molecular shape of the specific lipid dictates the way in which the phospholipids organize themselves in water [14]. PC, the most abundant phospholipid species in cell membranes of humans and other mammals, is cylindrical in shape and tends to form a bilayer structure when dispersed in water, with the hydrophobic tails pointing inward. Lysophosphatidylcholine (LPC) has an identical head group to PC, but has only one fatty acid attached. As a result, the molecular shape is an inverted cone, which is advantageous in forming a micellar structure. PE, on the other hand, has a smaller headgroup, resulting in an overall conical shape. These molecules tend to form an inverted hexagonal structure with hydrophilic heads clustered together, see FIG. 4

In nature, phospholipids are found as combinations of multiple species. In humans, PC and PE are the most abundant species found in cell membranes [15]. The non-bilayer lipids do not form membranes on their own, but their existence next to PC yields an evolutionary advantage by facilitating transport through the membrane [16] and fusion of the membranes [17, 18]. Including differently sized head groups in the bilayer relieves the lateral stress across the headgroup while increasing the chain pressure, thereby allowing room for external binding while enhancing the membrane integrity [14]. The polyunsaturated long-chain fatty acids in krill PC further impact the curvature stress of the dispersed particles when formulated, increasing fluidity and permeability through the membranes or micelles.

The formulation capacity of phospholipids is remarkably high. In the parenteral nutrition product Intralipid®, 200 g of soybean oil (TG) is emulsified with 1.2 g phosphatidylcholine to 1000 g in water/glycerin. Krill phospholipids also prove to be an excellent emulsifier for triglycerides and other hydrophobic molecules. When processed properly, krill phospholipids form an emulsion with no tailing in its particle size distribution, indicating a long shelf life and maximum surface area for improved absorption.

Furthermore, increased concentration of krill phospholipids renders advantage in stability of the emulsion. As described below, up-concentrated krill phospholipids are feasible. Combining the excellent dispersion properties of krill phospholipids with the added health benefits from PL-bound omega-3 fatty acids, krill phospholipids is a great candidate for formulating with absorption limited therapeutic molecules.

As discussed above, the marine phospholipids utilized in the methods and formulations of the present invention are preferably derived from a marine source such as krill, herring, squid or algae. In some preferred embodiments, the phospholipids are prepared as described in PCT/IB2016/000208 and PCT/US2016/017343, both of which are herein incorporated herein by reference in their entirety.

Starting Materials for Production of Phospholipids

A variety of materials may be utilized to prepare the phospholipids utilized in the methods and formulations of the present invention. The biological starting material may preferably be or be produced from an algal biomass or marine animal biomass. In preferred embodiments, marine animal biomasses are utilized as the starting material. Suitable marine animal biomasses include, but are not limited to, krill, crabs, Calanus, plankton, eggs, crayfish, shrimp, fish, especially herring, molluscs (including cephalopods such as squid). The biological starting material can be either fresh or frozen, or can be a material produced from an algal, plant or marine animal biomass such as a meal, powder, hydrolysate, or coagulate (paste). The paste may be a wet paste or a dried paste. In some preferred embodiments, the biological starting material is a krill material, for example a krill meal, krill hydrolysate, krill coagulate, or fresh or frozen krill. Any species of krill may be utilized. In preferred embodiments, the krill is *Euphausia superba* or *Euphausia pacifica.*

In some particularly preferred embodiments, the biological starting material is a krill meal. Krill meal can preferably be made by any standard marine meal process. In general, the krill meal is produced by cooking freshly caught krill at low temperature (approximately 80-85° C.) and drying to reduce the moisture content to approximately 5 to 8% and then grinding. In embodiments where the product is intended for human consumption, it is preferable to pack and store the meal under nitrogen without the addition of antioxidants.

Accordingly, the processes of the present invention may be used with a wide variety of starting materials. The remainder of the discussion of the processes generally refer to the use of krill meal as the starting material. However, it will be understood that any of the starting materials considered herein may be substituted for krill meal in the described processes.

Solvent extraction From Krill Meal

In the first step of the extraction process, the krill meal is mixed with a suitable solvent to extract lipids from the meal. In contrast to prior art methods, the present invention utilizes conditions which preferably extract the maximum amount of lipids from the krill meal at the cost of an increased amount of contaminants in the initial solvent extract. In preferred embodiments, the solvent is an organic protic solvent, however other solvents known for use in extraction of food grade lipids may also be used such as acetone, hexane, etc. Suitable organic protic solvents include, but are not limited to, n-butanol, n-propanol, isopropanol, nitromethane, ethanol, and methanol. In particularly preferred embodiments, the protic solvent is ethanol.

In preferred embodiments, the concentration of the protic solvent used in the initial solvent extraction step is at least 90%, or preferably from about 94% to 98%, more preferably from about 95% to 97%, and is most preferably about 96% (e.g., 96% ethanol or methanol).

In some embodiments, the protic solvent is mixed with the biological starting material at a ratio of protic solvent: biological starting material of about 1:1 to 10:1, preferably about 3:1 to 6:1, more preferably about 4:1 to 5:1, and most preferably about 4.4:1.

In preferred embodiments, the biological starting material is extracted with protic solvent at a temperature of from about 5° C. to 65° C., from about 20° C. to about 60° C., preferably from about 30° C. to 50° C., more preferably from about 30° C. to 50° C., and most preferably at about 40° C. In some embodiments, the extraction time (i.e., the amount of time the biological starting material is in contact with the solvent) is from about 10 minutes to about 2 hours, preferably from about 15 minutes to 60 minutes, more preferably from about 20 minutes to about 45 minutes, and most preferably about 30 minutes.

Following the extraction step, a crude krill lipid solution containing the soluble lipids from the krill meal is separated from the solvent/krill meal mixture, for example by decantation and or filtration. The insoluble material, comprising proteins and other useful materials is then dried to recover ethanol. The remaining protein-rich meal product may subsequently be used in food products, protein supplements, animal feeds and the like. In some embodiments, the decanted solution containing soluble lipids has a dry matter content of from about 4% to 9% w/w, preferably from about 5.5% to 7.5% w/w, and most preferably from about 6% to 7% w/w, where w/w refers to the weight of dry matter as a percent of the total solution weight. In preferred embodiments, the dry matter consists essentially of crude krill lipids, and preferably has a lipid content of greater than 90%, 95%, 96%, 97%, 98% or 99% w/w, wherein w/w refers to the weight of lipids a percent of the total dry matter weight.

Desalting

In some embodiments, the crude krill lipid solution is desalted to remove hexane insoluble materials such as insoluble inorganic salts (e.g., NaCl with small or trace amounts of KCl and/or $AlCl_3$) as well as unwanted compounds such as trimethylamine oxide, and metals such as copper and arsenic.

In some embodiments, the crude krill lipid solution is desalted by evaporating the solvent from crude krill lipid solution to provide a crude krill lipid composition and then subjecting the crude krill lipid composition to repeated washes with an aqueous solvent. Suitable aqueous solvents include, but are not limited to, ethanol blended with water or deionized water so that the ethanol concentration is from about 40% to 70%, preferably about 50% to 60%. In these embodiments, the crude krill lipid composition is mixed with the solvent, the lipid phase is recovered, and the aqueous phase is decanted. The washing step may be repeated as needed, for example 1, 2, 3, 4, 5 or more times. The ration of aqueous solvent: crude krill lipid composition is preferably from about 1:1 to 1:5 for each wash step, more preferably from about 1:1 to 2.5:1, and most preferably about 1:1.7.

In some embodiments, the crude lipid solution is desalted by chromatography. Suitable chromatographic media include silica gel media, including but not limited to spherical silica gels and derivatized silica gels such as C8 (octyl functionalized silica) and C18 (octadecyl functional silica) and ion exchange resins such as Dowex™ resins. In embodiments where chromatography is utilized, the crude krill lipids are preferably applied to the chromatographic medium in a protic solvent, preferably the same solvent used in the initial extraction (e.g., ethanol). Standard column chromatography methods may be utilized, however, moving bed chromatography or simulated moving bed chromatography apparatuses may preferably be utilized.

The composition of the desalted krill lipids on a dry matter basis may be preferably characterized as follows. In some embodiments, the desalted krill lipids preferably comprise from about 30% w/w to 65% w/w phospholipids, more preferably from about 40% w/w to about 65% w/w phospholipids, and most preferably about 58% w/w phospholipids, wherein w/w refers to the weight of the phospholipids as a percent of the total desalted kill lipid weight. In some embodiments, the desalted krill lipids preferably comprise from about 32% w/w to 52% w/w triglycerides, more preferably from about 36% w/w to about 48% w/w triglycerides, and most preferably about 42% w/w triglycerides, wherein w/w refers to the weight of the triglycerides as a percent of the total desalted krill lipid weight. In some embodiments, the desalted krill lipids preferably comprise from about 3% w/w to 13% w/w free fatty acids, more preferably from about 5% w/w to about 11% w/w free fatty acids, and most preferably about 8% w/w free fatty acids, wherein w/w refers to the weight of the free fatty acids as a percent of the total desalted krill lipid weight. In some embodiments, the desalted krill lipids preferably comprise from about 0.5% w/w to 5% w/w lysophospholipids, more preferably from about 0.8% w/w to about 3.2% w/w lysophospholipids, and most preferably about 1.2% to 2.8% w/w lysophospholipids, wherein w/w refers to the weight of the lysophospholipids as a percent of the total desalted krill lipid weight. In some embodiments, the desalted krill lipids preferably comprise less than about 5% w/w inorganic salts, preferably less than about 1% w/w inorganic salts, more preferably less than about 0.5% w/w inorganic salts, even more preferably less than about 0.2% w/w w/w inorganic salts, and most preferably less than about 0.1% w/w inorganic salts, wherein w/w refers to the weight of the inorganic salts as a percent of the total desalted krill lipid weight. In some embodiments, the desalted krill lipids preferably comprise less than about 5 mg N/100 g, more preferably less than about 3 mg N/100 g, even more preferably less than about 2 mg N/100 g, and most preferably less than about 1 mg N/100 g, where the N content serves as a convenient proxy for trimethylamine oxide (TMAO) content. In some embodiments, the desalted krill lipids comprise less than about 10 ppm copper ($Cu^{++}$), more preferably less than about 5 ppm $Cu^{++}$, even more preferably less than about 2 ppm $Cu^{++}$, and most preferably less than about 1 ppm $Cu^{++}$. In some embodiments, the desalted krill lipids comprise less than about 10 ppm total arsenic ($As^{3+}$, organic and inorganic), more preferably less than about 5 ppm total arsenic, even more preferably less than about 3 ppm total arsenic, and most preferably less than about 1 ppm total arsenic. In some embodiments, the desalted krill lipids preferably comprise from about 0.01% to 2% w/w ethyl esters, more preferably from about 0.01% to about 1.5% w/w ethyl esters, and most preferably from about 0.01% to about 1% w/w ethyl esters, wherein w/w refers to the weight of the ethyl esters as a percent of the total desalted krill lipid weight. In some embodiments, the krill phospholipid concentrate preferably comprise less than about 5%, 4%, 3% or 2% w/w ethyl esters down to a lower limit of 0.01% ethyl esters (i.e., between 5% and 0.01% w/w ethyl esters, between 4% and 0.01% w/w ethyl esters, between 3% and 0.01% w/w ethyl esters, or between 2% and 0.01% w/w ethyl esters), more preferably less than about 1.5% w/w ethyl esters, and most preferably less than about 1% w/w ethyl esters, wherein w/w refers to the weight of the ethyl esters as a percent of the total desalted krill lipid weight. In some embodiments, the desalted krill lipids have a conductivity of less than about 50 μS/cm when measured with 5% dry matter in 95% ethanol, more preferably a conductivity of less than about 30 μS/cm when measured with 5% dry matter in 95% ethanol, and most preferably a conductivity of less than about 20 μS/cm when measured with 5% dry matter in 95% ethanol. In some embodiments, the desalted krill lipids have a viscosity of from about 50 to 800 mPas at 25° C., more preferably from about 100 to 400 mPas at 25° C., and most preferably 180 to 340 mPas at 25° C. In some embodiments, the desalted krill lipid compositions have a pH of from about 6.7 to 8.3 when measured in 95% ethanol.

Phospholipid Concentration

In some embodiments, the present invention provides methods for concentrating lipids (e.g., neutral lipids or polar lipids such as phospholipids) in a solution. While the methods are described in reference to the desalted krill lipids described above, the methods are generally applicable to any lipid fractions that contain phospholipids.

Accordingly, in some embodiments, the dry matter content of a lipid composition containing phospholipids is adjusted to a predetermined level by adding or removing solvent and the resulting is allowed to fractionate so that the phospholipids are predominantly partitioned into one phase and the neutral lipids partitioned into a different phase. In some embodiments, a lipid composition containing phospholipids such as the desalted krill lipids is mixed with a suitable protic solvent, preferably ethanol, so that the dry matter (i.e., lipid) content of the resulting solution is from about 10% to 40% w/w, preferably about 15% to 35% w/w, more preferably about 18% to 30% w/w, and most preferably about 20% to 25% w/w. In embodiments where the desalting step already provides the lipids in a suitable protic alcohol solution, such as is the case where ethanol is used as the solvent for chromatography, the desalted krill lipid solution may preferably be evaporated to provide desired dry matter content, i.e., from about 10% to 40% w/w, preferably about 15% to 35% w/w, more preferably about 18% to 28% w/w, and most preferably about 20% to 22% w/w. Suitable methods for evaporation include, but are not limited to, evaporation under reduced pressure (e.g., vacuum distillation), falling film evaporation, and removal of solvents via a membrane.

Following adjustment of the dry matter content to the desired level by either adding or removing solvent, the solution is then allowed to fractionate into an upper, light phase solution with an enhanced phospholipid content and a lower, heavy phase solution containing predominantly neutral lipids and a high level of astaxanthin. Preferably, the temperature of the solution during the fractionation step is controlled. In some embodiments, the temperature for the fractionation step is from about 0° C. to about 20° C., preferably from about 5° C. to about 15° C., more preferably from about 8° C. to about 12° C., and most preferably about 10° C.

In some embodiments, the concentration of the protic solvent may be varied in order to control the phospholipid concentration in the lipid composition of the upper phase. In some embodiments, the protic solvent has a concentration of from about 55% to 100%, more preferably about 65% to 98%. In some preferred embodiments, the protic solvent has a concentration of from about 90% to 100%, more preferably about 92% to 98%, and most preferably about 95%. In these embodiments, the phospholipid content on a dry matter basis of the lipids in the upper phase after fractionation is from about 50% to 70% w/w, preferably about 55% to 65% w/w and most preferably about 60% w/w. In still other preferred embodiments, the protic solvent has a concentration of from about 80% to 90% w/w, more preferably about 82% to 88% w/w, and most preferably about 85% w/w. In these embodiments, the phospholipid content on a dry matter basis of the lipids in the upper phase after fractionation is from about 70% to 90% w/w, preferably about 75% to 85% w/w and most preferably about 80% w/w.

In some embodiments, the upper and lower phases are separated by centrifugation, preferably cryocentrifugation with a two phase or three phase separator. In some embodiments, the centrifugation is conducted at from about 0° C. to about 30° C., more preferably from about 0° C. to about 10° C. and most preferably from about 3° C. to about 7° C. In general, the gravitational force utilized will depend on delta T between the phases. Lower temperatures provide a greater delta T. In some preferred embodiments, the G force employed in the separation is from about 8000×G to about 15000×G.

In some embodiments, the process steps of adjusting the dry matter content as described above through the centrifugation steps are repeated one or more times.

In some embodiments, the upper light phase is collected and processed further. The solvent is preferably removed from the upper phase by one or more evaporation steps to yield a krill phospholipid concentrate. The krill phospholipid concentrates preferably comprise from about 50% to 85% w/w total phospholipids, and more preferably from about 55% to 80% w/w total phospholipids, and most preferably about 52% to 60% w/w total phospholipids, wherein w/w refers to the weight of phospholipids as a percent of the total weight of the concentrate.

In some embodiments, the lower heavy phase is collected and processed further. In some embodiments, the solvent is removed from the lower phase to provide a krill neutral lipid concentrate. In some embodiments, the lower phase may be fractionated with protic solvent and subjected to a second centrifugation step to recover additional phospholipids not recovered in the first fractionation step. Again, the solvent is removed from the resulting lower phase to provide a krill neutral lipid concentrate. The krill neutral lipid concentrate in both instances is characterized in containing high levels of astaxanthin. In some embodiments, the krill neutral lipid concentrate may be combined or blended with the krill phospholipid concentrate to provide a lipid composition with desired levels of phospholipids, neutral lipids, and astaxanthin. In some embodiments, the krill neutral lipid concentrate may be further processed (e.g., by chromatography) to provide an astaxanthin concentrate. The astaxanthin concentrate may then be combined or blended with the krill phospholipid concentrate to provide a lipid composition with desired levels of phospholipids and astaxanthin.

In some embodiments, the krill phospholipid concentrates on a dry matter basis preferably comprise from about 5% w/w to 35% w/w triglycerides, more preferably from about 10% w/w to about 30% w/w triglycerides, and most preferably about 15% to 25% w/w triglycerides, wherein w/w refers to the weight of the triglycerides as a percent of the total krill phospholipid concentrate weight. In some embodiments, the krill phospholipid concentrates preferably comprise from about 2% w/w to 13% w/w free fatty acids, more preferably from about 4% w/w to about 11% w/w free fatty acids, and most preferably about 4% to 10% w/w free fatty acids, wherein w/w refers to the weight of the free fatty acids as a percent of the total krill phospholipid concentrate weight. In some embodiments, the krill phospholipid concentrates preferably comprise from about 0.5% w/w to 10% w/w lysophospholipids, more preferably from about 0.8% w/w to about 7.0% w/w lysophospholipids, and most preferably less than about 5.0% w/w or 3.0% w/w lysophospholipids, wherein w/w refers to the weight of the lysophospholipids as a percent of the total krill phospholipid concentrate weight. In some embodiments, the krill phospholipid concentrates preferably comprise less than about 5% w/w inorganic salts, preferably less than about 1% w/w inorganic salts, more preferably less than about 0.5% w/w inorganic salts, even more preferably less than about 0.2% w/w inorganic salts, and most preferably less than about 0.1% or 0.05% w/w inorganic salts, wherein w/w refers to the weight of the inorganic salts as a percent of the total krill phospholipid concentrate weight. In some embodiments, the krill phospholipid concentrate preferably comprises less than about 5 mg N/100 g, more preferably less than about 3 mg N/100 g, even more preferably less than about 2 mg N/100 g, and most preferably less than about 1 mg N/100 g TMAO, where the N content serves as a convenient proxy for trimethylamine oxide (TMAO) content. In some embodiments, the krill phospholipid concentrates comprise less than about 10 ppm copper ($Cu^{++}$), more preferably less than about 5 ppm $Cu^{++}$, even more preferably less than about 2 ppm $Cu^{++}$, and most preferably less than about 1 ppm $Cu^{++}$. In some embodiments, the krill phospholipid concentrates comprise less than about 10 ppm total arsenic ($As^{3+}$), more preferably less than about 5 ppm total arsenic, even more preferably less than about 3 ppm total arsenic, and most preferably less than about 1 ppm total arsenic. In some embodiments, the krill phospholipid concentrates preferably comprise from about 0.01% to 2% w/w ethyl esters, more preferably from about 0.01% to about 1.5% w/w ethyl esters, and most preferably from about 0.01% to about 1% w/w ethyl esters, wherein w/w refers to the weight of the ethyl esters as a percent of the total krill phospholipid concentrate weight. In some embodiments, the krill phospholipid concentrate preferably comprise less than about 5%, 4%, 3% or 2% w/w ethyl esters down to a lower limit of 0.01% ethyl esters (i.e., between 5% and 0.01% w/w ethyl esters, between 4% and 0.01% w/w ethyl esters, between 3% and 0.01% w/w ethyl esters, or between 2% and 0.01% w/w ethyl esters), more preferably less than about 1.5% w/w ethyl esters, and most preferably less than about 1% w/w ethyl esters, wherein w/w refers to the weight of the ethyl esters as a percent of the total krill phospholipid concentrate weight. In some embodiments, the krill phospholipid concentrate has a conductivity of less than about 50 μS/cm when measured with 5% dry matter in 95% ethanol, more preferably a conductivity of less than about 30 μS/cm when measured with 5% dry matter in 95% ethanol, and most preferably a conductivity of less than about 20 μS/cm, 10 μS/cm, 5 μS/cm or 1 μS/cm when measured with 5% dry matter in 95% ethanol. In some embodiments, the krill phospholipid concentrate has a viscosity of from about 400 to 2000 mPas at 35° C., more preferably from about 500 to 1800 mPas at 35° C., and most preferably from about 600 to 1600 mPas at 35° C. In some embodiments, the krill phospholipid concentrate has a pH of from about 6.7 to 8.3 when measured in 95% ethanol. In this section, we present the ways in which krill phospholipids could be utilized to maximize the health benefits of some lipophilic dietary supplements with low absorption.

CBD

Cannabidiol (CBD) is a non-psychotropic phytocannabinoid from the Cannabis sativa plant, also known as cannabis or hemp. In the US, purified CBD is approved as a treatment of seizures associated with Lenox-Gastaut syndrome or Dravet syndrome [19, 20]. Clinical trials are ongoing for indications such as anxiety, schizophrenia, addiction, post-traumatic disorder, and cancer [21]. Although multiple health benefits of CBD is promising, delivering CBD to the site of action is a challenge due to its poor bioavailability, around 6% in humans when taken orally [22]. CBD is extremely lipophilic and hardly soluble in water, resulting in poor gastrointestinal absorption [23]. Accordingly, CBD is a BCS class II drug, with a low water solubility and high permeability to the cell membrane. Low bioavailability generally leads to suboptimal therapeutic efficacy while also producing high inter-individual variability in pharmacokinetics [24]. As a result, fluctuating dose is a problem for CBD and increased bioavailability will improve the dosing consistency.

Figure 5:
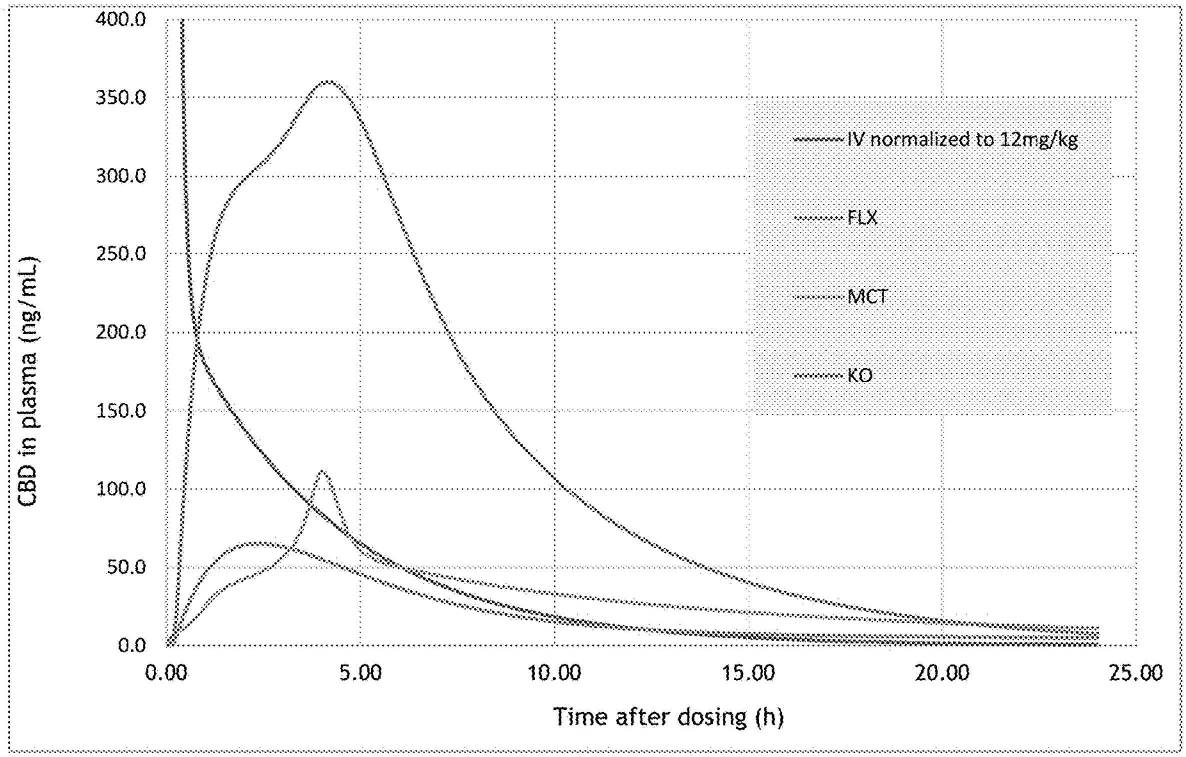
FIG. 5. Plasma CBD concentration after dosing. Krill oil (KO) can increase the absorption of CBD to a much greater extent than blending medium chain triglyceride (MCT) oil.

Lipid based formulations can help with the solubility of lipophilic CBD [25], thereby increasing the bioavailability. Therefore, CBD oils are commonly sold in carrier oils such as medium chain triglyceride (MCT) oil, hemp seed oil, olive oil, and avocado oil, with MCT oil being the most common. Krill oil is a better option as a bioavailability enhancer for lipophilic products, due to the amphiphilicity of phospholipids. As FIG. 5 shows, krill oil increases the bioavailability of CBD by 3-fold compared to the market leading MCT. Furthermore, the omega-3 fatty acids in krill oil may assist CBD in vivo to maximize the health benefits. The human endocannabinoid system is involved in the regulation of energy balance. The system includes CB1, CB2, the endogenous agonists known as endocannabinoids (ECs), and enzymes for biosynthesis and degradation of ECs [26-28]. CBD does not work directly on the human endocannabinoid system but is thought to influence the system by mimicking the body's own endocannabinoids. Endocannabinoids are lipid-based signaling molecules that are synthesized internally from omega-3 and omega-6 fatty acids [29]. Hence, krill phospholipids are ideal carriers for CBD as they combine the absorption enhancing ability and the omega-3 fatty acid supplementation.

Curcumin

Curcumin is a bright yellow polyphenol derived from Curcuma longa (turmeric). The medicinal use of turmeric plant has been ongoing in India and China for thousands of years for indications like muscular disorders, arthritis, hepatitis, etc. [30]. More recently, pre-clinical and clinical investigation of curcumin as therapeutic agents began in early 2000, focusing primarily on its anti-inflammatory and anticancer effects following oral or topical administration [31, 32]. However, the biggest challenge in successfully achieving biological effect using curcumin is its low systemic bioavailability. Human clinical studies have indicated that curcumin exhibits a low bioavailability following oral application, with its metabolites detectable in plasma and urine with daily doses as high as 3600-12000 mg [31].

Figure 6:
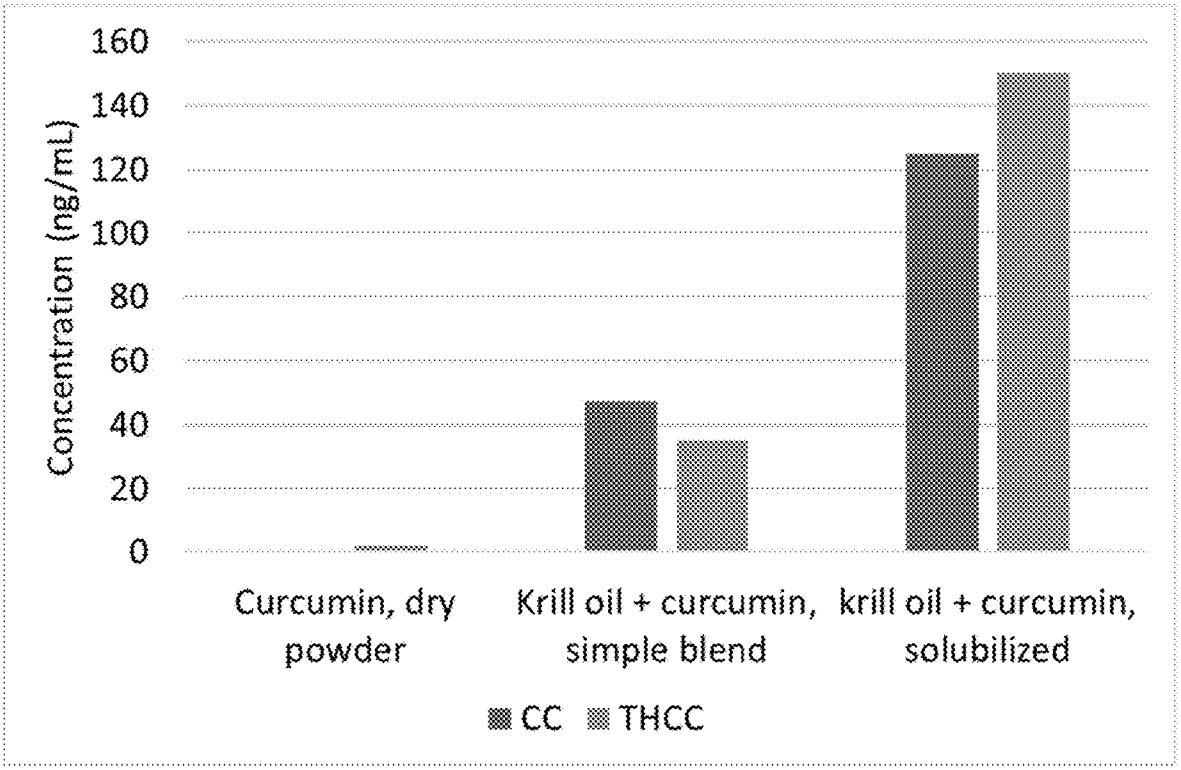
FIG. 6. Permeated curcuminoids, Caco-2 in vitro results, normalized to 100 mg of curcumin (CC). THCC is tetrahydrocurcuminoid, a metabolite of curcumin.
Figure 7:
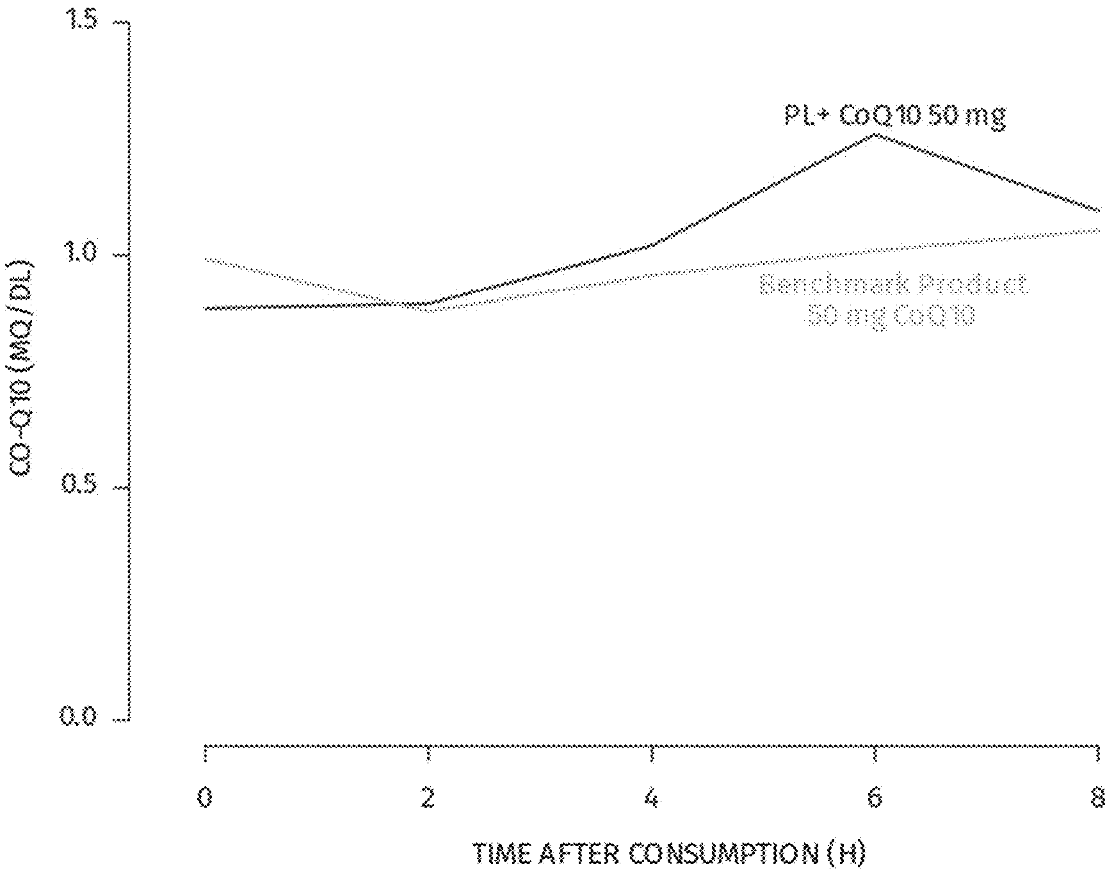
FIG. 7. Plasma bioavailability of CoQ10 formulated with PL from krill oil compared to benchmark CoQ10-product.

Curcumin's low bioavailability is attributed to low solubility in aqueous solutions as well as instability in physiological pH [33]. Curcumin is classified as a biopharmaceutical classification system (BCS) class IV molecule on the basis of its poor aqueous solubility (11 ng/ml in aqueous buffer pH 5) and permeability through intestinal epithelial cells. Different formulation strategies have emerged to improve the bioavailability of curcumin, including incorporation into nanoparticles, liposomes, micelles, nano/micro-emulsions, and solid dispersions [34]. Phospholipids from krill oil have also been utilized as curcumin carriers, either in the form of nano-emulsions or liposomes [35-37]. As disclosed in Example 2, the effectiveness of krill oil in improving the bioavailability of curcumin is demonstrated in the Caco-2 cell system. The Caco-2 cell system is a well characterized in vitro model for evaluating permeability through the intestinal barrier [38]. When dry curcumin powder is compared with simple-blended 60% krill oil and 40% curcumin mixture, the transepithelial transport of curcumin was increased with krill oil as shown in FIG. 6. The absorption characteristics of curcumin can be further improved in combination of krill oil with processing techniques to improve the solubility even more. Solubilizing the curcumin in krill oil using a food-grade solvent dissolution and evaporation results in an even higher permeability than the dry powder, possibly allowing for a formulation that is lower in curcumin concentration while achieving greater health benefits.

$CoQ_{10}$

Coenzyme $Q_{10}$ ($CoQ_{10}$) is a fat-soluble, vitamin-like substance that is primarily consumed in relation to suboptimal cellular energy and oxidative injury due to its role in the oxidative phosphorylation in mitochondria [39, 40]. $CoQ_{10}$ is endogenously synthesized in our bodies, but the level of $CoQ_{10}$ decreases in certain tissues as we age. Exogenous supplementation of $CoQ_{10}$ has shown therapeutic benefits for age-related disease in animal and human studies especially the ones related to oxidative stress such as cardiovascular and metabolic diseases [41, 42].

The degree of therapeutic effects of $CoQ_{10}$ largely depends on the bioavailability and tissue uptake. However, the high molecular weight and lipophilicity of $CoQ_{10}$ results in low water solubility and therefore low systemic availability [43, 44]. It is classified as a biopharmaceutical class II compound with low solubility but good permeability. The bioavailability of $CoQ_{10}$ varies greatly depending on the type of formulation. In one screening study, $CoQ_{10}$ dispersed in oils showed the greatest bioavailability in general [45]. In fact, formulation of $CoQ_{10}$ in krill oil can increase the bioavailability for up to 25-fold. In addition to the dispersion effect from the phospholipids, the omega-3 fatty acids in krill oil are also thought to assists in improving the bioavailability.

Compounds From Flavonoid Family

Fisetin and Quercetin are examples of dietary antioxidants explored for their health benefit, particularly as an anticancer phytoconstituent and to slow degenerative aging processes. Fisetin has been shown to 1) Function as a senolytic, clearing away dysfunctional senescent cells and allowing healthy cells to thrive, 2) Protect the brain in various models of neurodegenerative disorders, 3) Improve outcomes in people who have suffered strokes, 4) Help prevent malignant changes in cells, and 5) Help fight obesity and type II diabetes. Quercetin has also been suggested to have senolytic effects and to reduce inflammatory responses, due to its ability to reduces the activity of nuclear factor kappa B (NF-κB), a pro-inflammatory molecule.

Fisetin and Quercetin belong to the family of flavonoids, which are found in various fruits and vegetables. Fisetin exhibits poor aqueous solubility and hence poor bioavailability. Fisetin is Class II drug according to BCS classification, its low solubility (<1 mg/mL) and its low bioavailability are the limiting factors of its administration in vivo. Quercetin also exhibits low absorption due to poor aqueous solubility. Quercetin is found to be a class IV-based compound in accordance to BCS (Biopharmaceutical Classification System). It exhibits poor aqueous solubility and poor oral absorption even when ingested in large amount. Chemically, Fisetin and Quercetin are comparable to curcumin and their bioavailability is expected to increase similarly if formulated correctly with krill oil phospholipids, as seen with curcumin, CoQ10 and CBD oil.

| | | |
|---|---|---|
| | 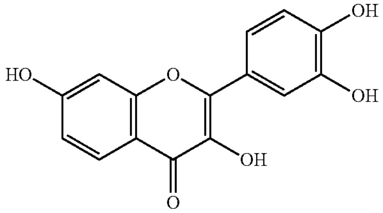 [SMILES: O=c1c(O)c(-c2ccc(O)c(O)c2)oc2cc(O)ccc12] | 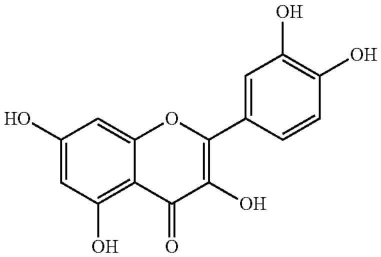 [SMILES: O=c1c(O)c(-c2ccc(O)c(O)c2)oc2cc(O)cc(O)c12] |
| Compound | Fisetin | Quercetin |
| logP | 1.81-2.03 | 1.50 |
| Solubility water | 0.15 mg/mL | 0.06 mg/mL |
| Solubility ethanol | 5 mg/mL | 2 mg/mL |

The senolytic effect of fisetin has been linked to improvement of long-term memory and reduction of cognitive decline.

EPA & DHA

Omega-3 fatty acids are polyunsaturated fatty acids that are essential in cellular structure and function. The main bioactive omega-3 fatty acids, which have been described extensively, are eicosapentaenoic acid (EPA or 20:5n3) and docosahexaenoic acid (DHA or 22:6n-3). EPA consists of 20 carbons and 5 double bonds and can be converted enzymatically into DHA. DHA has 22 carbons and 6 double bonds. They are called omega-3 fatty acids because they have their last double bond three carbon atoms from the methyl end. In comparison, an omega-6 fatty acids have their last double bond 6 carbon atoms from the methyl end. Deficiency in omega-3 or imbalance between omega-3 and omega-6 fatty acids are associated with heart diseases and inflammatory diseases [20-22]. Omega-3 fatty acids are also important for maintaining mental health and brain development and function [23].

The typical western diet is abundant in omega-6 fatty acids compared to omega-3 fatty acids, and the balance between the two is highly disturbed [24, 25]. In fact, most people have mean intake levels below the optimal daily EPA and DHA dose of 250 mg recommended by the World Health Organization (WHO) and the European Food Safety Authority (EFSA) and could therefore benefit from omega-3 supplementation.

Supplementary omega-3 fatty acids come primarily in three different forms, omega-3 phospholipids, omega-3 triglycerides and omega-3 ethyl-esters. Triglycerides have 3 fatty acids connected to the glycerol backbone, whereas phospholipids incorporate two fatty acids and a hydrophilic head group. Omega-3s can also come in the form of ethyl esters, where the fatty acids are each singularly attached to an ethanol head group. Krill oil has EPA and DHA omega-3 fatty acids primarily bound as phospholipids and is known to increase the Omega-3 Index to a greater extent compared to fish oil, which is rich in the triglyceride form of omega-3. Omega-3 in the form of ethyl esters is even more inferior to the triglycerides of fish oil [26]. Krill oil also performs better in modulating the blood triglyceride levels, a key biomarker for heart disease [27].

The differential effect of phospholipid omega-3 and triglyceride omega-3 is as follows; Triglycerides are highly insoluble in water and are therefore totally dependent on bile and formation of micelles for digestion and absorption. The bile facilitates micelle formations which is necessary for proper absorption of fats and fat-soluble nutrients. Micelles are formed using a combination of compounds with fat soluble (hydrophobic) and water soluble (hydrophilic) properties. Emulsification of triglycerides by bile salts makes them accessible for digestion by enzymes. The digested triglycerides form micelles, particles that make fatty acid absorption possible, together with bile before they are ready for absorption in the small intestine.

Phospholipids are not dependent on bile for digestion, because they have the ability of forming water soluble complexes, such as micelles, on their own, see Table 1. Phospholipids may be absorbed without digestion in the intact form, or as lysophosphatidylcholine after digestion by enzymes in the small intestine. The limited requirement for digestion in the small intestine before absorption leads to the suggestion that omega-3 phospholipids have increased availability in the human body [28-35].

Furthermore, clinical evidence suggests that emulsifying omega-3 oil prior to ingestion increases the absorption of longer chain unsaturated fatty acids [36, 37]. As shown by Example 1, TG or EE forms of omega-3 can be emulsified into more fine particles with an even size distribution when combined with phospholipids of krill oil.

Krill oil is rich in amphiphilic phospholipid molecules linked to omega-3 fatty acids. While the PL-EPA and PL-DHA are great supplements in and of themselves for maintaining brain, eye, and cardiovascular health, they are also excellent for formulating bioactive compounds that are poorly soluble in water. In an aqueous environment, the phospholipids form micellar or liposomal structures, carrying the insoluble compound with it and delivering it to the inner lining of the intestines to be absorbed. Lipophilic substances, such as EPA and DHA, CBD, curcumin and $CoQ_{10}$, as well as flavonoids including Fisetin and Quercetin, could benefit tremendously in bioavailability when formulated with PL from krill oil or other marine sources.

It is established that reduced levels of EPA and DHA are associated with cognitive decline, and generally that EPA and DHA are important for maintaining mental health and brain development and function. It has further been demonstrated that transport of EPA and DHA to the brain is done in the PL form, specifically the lysophosphatidylcholine, LPC. Hence, for the purpose of improving mental health, the PLs from krill oil, and particularly PC and LPC, are ideal carriers for enhancing uptake of compounds like fisetin, thereby combining increased bioavailability of fisetin as well as transport of EPA/DHA to the brain.

In a first aspect of the invention, it is provided a formulation comprising marine phospholipid molecules in combination with therapeutic ingredients selected from the group consisting of a lipophilic substance and substances classified as Biopharmaceutical classification system (BCS) class 2, 3, or 4. Suitable lipophilic substances include, but are not limited to omega-3 fatty acids forms and lipophilic bioactive components. In some particularly preferred embodiments, the therapeutic ingredients are selected from the group comprising fish oil concentrates (triglyceride form), omega-3 ethyl esters, CBD, curcumin, CoQ10, fisetin and quercetin. In some preferred embodiments, the formulation comprises greater than 17% w/w of the phospholipid molecules, wherein w/w refers to the weight of the phospholipid molecules divided by the total weight of the formulation. In some preferred embodiments, the phospholipid molecule portion of the formulation is further characterized in comprising greater than 80% phosphatidylcholine and having more than 25% omega-3 moieties attached to the phospholipid molecules on a molar basis.

In some preferred embodiments, the mixture forms an emulsion with a droplet size of less than 600 nm in an artificial stomach fluid, more preferred the mixture forms an emulsion with a droplet size of less than 500 nm in an artificial stomach fluid, even more preferred the mixture forms an emulsion with a droplet size of less than 400 nm in an artificial stomach fluid, even more preferred the mixture forms an emulsion with a droplet size of less than 300 nm in an artificial stomach fluid, even more preferred the mixture forms an emulsion with a droplet size of less than 200 nm in an artificial stomach fluid.

In some preferred embodiments, the mixture forms an emulsion with a droplet size of from 150 to 600 nm in an artificial stomach fluid, even more preferred the mixture forms an emulsion with a droplet size of from 150 to 500 nm in an artificial stomach fluid, even more preferred the mixture forms an emulsion with a droplet size of from 150 to 400 nm in an artificial stomach fluid, even more preferred the mixture forms an emulsion with a droplet size of from 150 to 300 nm in an artificial stomach fluid, even more preferred the mixture forms an emulsion with a droplet size of from 150 to 250 nm in an artificial stomach fluid. In some preferred embodiments, the mixture forms an emulsion with an average droplet size of from 150 to 600 nm in an artificial stomach fluid, even more preferred the mixture forms an emulsion with an average droplet size of from 150 to 500 nm in an artificial stomach fluid, even more preferred the mixture forms an emulsion with an average droplet size of from 150 to 400 nm in an artificial stomach fluid, even more preferred the mixture forms an emulsion with an average droplet size of from 150 to 300 nm in an artificial stomach fluid, even more preferred the mixture forms an emulsion with an average droplet size of from 150 to 250 nm in an artificial stomach fluid.

In some preferred embodiments, the mixture forms an emulsion wherein at least 80% of the droplets, and more preferably 90% of the droplets have a droplet size of from 150 to 600 nm in an artificial stomach fluid, even more preferred the mixture forms an emulsion wherein at least 80% of the droplets, and more preferably 90% of the droplets have a droplet size of from 150 to 500 nm in an artificial stomach fluid, even more preferred the mixture forms an emulsion wherein at least 80% of the droplets, even more preferred the mixture forms an emulsion wherein at least 80% of the droplets, and more preferably 90% of the droplets have a droplet size of from 150 to 400 nm in an artificial stomach fluid, even more preferred the mixture forms an emulsion wherein at least 80% of the droplets, and more preferably 90% of the droplets have a droplet size of from 150 to 300 nm in an artificial stomach fluid, even more preferred the mixture forms an emulsion wherein at least 80% of the droplets, and more preferably 90% of the droplets have a droplet size of from 150 to 250 nm in an artificial stomach fluid, even more preferred the mixture forms an emulsion wherein at least 80% of the droplets, and more preferably 90% of the droplets have a droplet size of from 150 to 200 nm in an artificial stomach fluid.

In some preferred embodiments, the mixture forms an emulsion with an average droplet size of from 120 to 600 nm in an artificial stomach fluid, even more preferred the mixture forms an emulsion with an average droplet size of from 120 to 500 nm in an artificial stomach fluid, even more preferred the mixture forms an emulsion with an average droplet size of from 120 to 500 nm in an artificial stomach fluid, even more preferred the mixture forms an emulsion with an average droplet size of from 120 to 400 nm in an artificial stomach fluid, even more preferred the mixture forms an emulsion with an average droplet size of from 120 to 300 nm in an artificial stomach fluid, even more preferred the mixture forms an emulsion with an average droplet size of from 120 to 250 nm in an artificial stomach fluid, even more preferred the mixture forms an emulsion with an average droplet size of from 120 to 200 nm in an artificial stomach fluid.

In some preferred embodiments, the mixture forms an emulsion wherein at least 80% of the droplets, and more preferably 90% of the droplets have a droplet size of from 120 to 600 nm in an artificial stomach fluid, even more preferred the mixture forms an emulsion wherein at least 80% of the droplets, and more preferably 90% of the droplets have a droplet size of from 120 to 500 nm in an artificial stomach fluid, even more preferred the mixture forms an emulsion wherein at least 80% of the droplets, even more preferred the mixture forms an emulsion wherein at least 80% of the droplets, and more preferably 90% of the droplets have a droplet size of from 120 to 400 nm in an artificial stomach fluid, even more preferred the mixture forms an emulsion wherein at least 80% of the droplets, and more preferably 90% of the droplets have a droplet size of from 120 to 300 nm in an artificial stomach fluid, even more preferred the mixture forms an emulsion wherein at least 80% of the droplets, and more preferably 90% of the droplets have a droplet size of from 120 to 250 nm in an artificial stomach fluid, even more preferred the mixture forms an emulsion wherein at least 80% of the droplets, and more preferably 90% of the droplets have a droplet size of from 120 to 200 nm in an artificial stomach fluid.

In a second aspect of the invention, there is provided methods of enhancing the absorption of therapeutic ingredients selected from the group consisting of a lipophilic substance and substances classified as Biopharmaceutical classification system (BCS) class 2, 3, or 4 in a subject in need thereof comprising administering to the subject a mixture of marine phospholipid molecules and a therapeutic ingredient selected from the group consisting of a lipophilic substance and substances classified as Biopharmaceutical classification system (BCS) class 2, 3, or 4.from a source different from the source of the marine phospholipids. In some preferred embodiments, the mixture comprises greater than 17% w/w of the phospholipid molecules, wherein w/w refers to the weight of the phospholipid molecules divided by the total weight of the formulation. In some preferred embodiments, the phospholipid molecule portion of the formulation is further characterized in comprising greater than 80% phosphatidylcholine and having more than 25% omega-3 moieties attached to the phospholipid molecules on a molar basis. In some preferred embodiments, the mixture forms an emulsion with a droplet size of less than 500 nm in an artificial stomach fluid, more preferred the mixture forms an emulsion with a droplet size of less than 400 nm in an artificial stomach fluid, even more preferred the mixture forms an emulsion with a droplet size of less than 300 nm in an artificial stomach fluid, even more preferred the mixture forms an emulsion with a droplet size of less than 200 nm in an artificial stomach fluid. In some preferred embodiments, the droplet size is defined as described above in more detail.

In some preferred embodiments, the marine source of the phospholipid molecules is selected from the group consisting of krill, herring, squid and algae. In some particularly preferred embodiments, the marine source of the phospholipid molecules is krill.

In some preferred embodiments, the marine source of the phospholipid molecules is a marine oil. It is contemplated that when the marine source of the phospholipids is an oil, the oil will generally comprise a mixture of at least phospholipid and triglyceride molecules. It will be appreciated that when a marine oil is utilized in the lipid formulations, the amount of oil included in the formulations will be the amount that provides the phospholipid molecule content described above. In some particularly preferred embodiments, the marine oil is krill oil. In some preferred embodiments, greater than 60% (on a molar basis) of the omega-3 moieties in the marine oil are attached to the phospholipid molecules in the marine oil. In some preferred embodiments, greater than 70% (on a molar basis) of the omega-3 moieties in the oil are attached to the phospholipid molecules in the marine oil. In some preferred embodiments, greater than 75% (on a molar basis) of the omega-3 moieties in the oil are attached to the phospholipid molecules in the marine oil. In some preferred embodiments, from 60% to 90% (on a molar basis) of the omega-3 moieties in the oil are attached to the phospholipid molecules in the marine oil. In some preferred embodiments, from 73% to 83% (on a molar basis) of the omega-3 moieties in the oil are attached to the phospholipid molecules in the marine oil.

In some preferred embodiments, the formulation or mixture comprises from 17% to 70% w/w of the phospholipid molecules from the marine source. In some preferred embodiments, the formulation or mixture comprises from 20% to 60% w/w of the phospholipid molecules from the marine source. In some preferred embodiments, the formulation or mixture comprises from 30% to 50% w/w of the phospholipid molecules from the marine source. In some preferred embodiments, the formulation or mixture comprises from 35% to 45% w/w of the phospholipid molecules from the marine source. In some preferred embodiments, the formulation or mixture comprises from 37% to 43% w/w of the phospholipid molecules from the marine source. In some preferred embodiments, the formulation or mixture comprises from 38% to 42% w/w of the phospholipid molecules from the marine source. In some preferred embodiments, the formulation or mixture comprises from 39% to 41% w/w of the phospholipid molecules from the marine source.

In some preferred embodiments, the lipid formulation or mixture comprises from 2.5% to 50% w/w of the therapeutic ingredient selected from the group of lipophilic substances and substances classified as Biopharmaceutical classification system (BCS) class 2, 3, and 4 from a source different than the marine source of the phospholipid molecules. In some preferred embodiments, the lipid formulation or mixture comprises from 2.5% to 20% w/w of the therapeutic ingredient selected from the group of lipophilic substances and substances classified as Biopharmaceutical classification system (BCS) class 2, 3, and 4 from a source different than the marine source of the phospholipid molecules. In some preferred embodiments, the lipid formulation or mixture comprises from 15% to 50% w/w of the therapeutic ingredient selected from the group of lipophilic substances and substances classified as Biopharmaceutical classification system (BCS) class 2, 3, and 4 from a source different than the marine source of the phospholipid molecules. In some preferred embodiments, the lipid formulation or mixture comprises from 15% to 40% w/w of the therapeutic ingredient selected from the group of lipophilic substances and substances classified as Biopharmaceutical classification system (BCS) class 2, 3, and 4 from a source different than the marine source of the phospholipid molecules.

In some preferred embodiments, the lipophilic substance from a source different than the marine source of the phospholipid molecules is selected from the group consisting of ethyl esters, triglycerides and combinations thereof. In some preferred embodiments, the ethyl esters are selected from the group consisting of ethyl esters of DHA or EPA and combinations thereof. In some preferred embodiments, the triglycerides are a fish oil. In some preferred embodiments, the triglycerides are fish oil concentrate. As used herein, the term 'fish oil concentrate' refers to a fish oil lipid composition that has been processed to increase the omega-3 content as compared to the starting material. In some preferred embodiments, the formulation or mixture comprises from 16% to 50% w/w of the ethyl esters selected from the group consisting of eicosapentaenoic acid and docosahexaenoic acid and combinations thereof. In some preferred embodiments, the formulation or mixture comprises from 20% to 50% w/w of the ethyl esters selected from the group consisting of eicosapentaenoic acid and docosahexaenoic acid and combinations thereof. In some preferred embodiments, the formulation or mixture comprises from 25% to 35% w/w of the ethyl esters selected from the group consisting of eicosapentaenoic acid and docosahexaenoic acid and combinations thereof. In some preferred embodiments, the formulation or mixture comprises from 27% to 33% w/w of the ethyl esters selected from the group consisting of eicosapentaenoic acid and docosahexaenoic acid and combinations thereof. In some preferred embodiments, the formulation or mixture comprises from 28% to 32% w/w of the ethyl esters selected from the group consisting of eicosapentaenoic acid and docosahexaenoic acid and combinations thereof. In some preferred embodiments, the formulation or mixture comprises from 29% to 31% w/w of the ethyl esters selected from the group consisting of eicosapentaenoic acid and docosahexaenoic acid and combinations thereof. In some preferred embodiments, the formulation or mixture comprises from 20% to 50% w/w of the fish oil or fish oil concentrate. In some preferred embodiments, the formulation or mixture comprises from 25% to 35% w/w of the fish oil or fish oil concentrate. In some preferred embodiments, the formulation or mixture comprises from 27% to 33% w/w of the fish oil or fish oil concentrate. In some preferred embodiments, the formulation or mixture comprises from 28% to 32% w/w of the fish oil or fish oil concentrate. In some preferred embodiments, the formulation or mixture comprises from 29% to 31% w/w of the fish oil or fish oil concentrate.

In some preferred embodiments, the therapeutic ingredient selected from the group of lipophilic substances and substances classified as Biopharmaceutical classification system (BCS) class 2, 3, and 4 from a source different than the marine source of the phospholipid molecules is selected from the group consisting of a cannabidiol (CBD) compound, a coenzyme Q10 (CoQ10) or a ubiquinone compound, and a curcumin compound or a compound belonging to flavonoids, including Fisetin and Quercetin. In some preferred embodiments, the therapeutic ingredient selected from the group of lipophilic substances and substances classified as Biopharmaceutical classification system (BCS) class 2, 3, and 4 from a source different than the marine source of the phospholipid molecules is a CBD compound and the lipid formulation or mixture comprises from 2.5% to 7.5% w/w the CBD compound. In some preferred embodiments, the therapeutic ingredient selected from the group of lipophilic substances and substances classified as Biopharmaceutical classification system (BCS) class 2, 3, and 4 from a source different than the marine source of the phospholipid molecules is a CoQ10 compound and the lipid formulation or mixture comprises from 15% to 25% w/w the CoQ10 compound. In some preferred embodiments, the therapeutic ingredient selected from the group of lipophilic substances and substances classified as Biopharmaceutical classification system (BCS) class 2, 3, and 4 from a source different than the marine source of the phospholipid molecules is a curcumin compound and the lipid formulation or mixture comprises from 15% to 25% w/w the curcumin compound.

EXAMPLES

Example 1

The purpose of this study was to evaluate the emulsifying properties of krill oil (KO), fish oil (FO) triglycerides (TG), fish oil ethyl esters (EE) and mixtures hereof in relation to gastrointestinal digestibility and absorption/performance. The krill oil used in this experiment was SUPERBA Boost, with a content of 58% w/w of phospholipids (see Table 3 for specifications). SUPERBA Boost further comprise neutral lipids (on average about 30% w/w), mostly in the form of TG (>20% w/w) and some free fatty acids (<8% w/w), monoglycerides, diglycerides and cholesterol.

Materials

TABLE 2

Materials used in this study.

| Generic name | Supplier | Quality | Batch no. |
|---|---|---|---|
| SUPERBA Boost ® (KO) | Aker BioMarine | — | A102145 |
| EPAX ® 2050 TGN (TG) | Epax Norway AS | — | 2021000752 |
| EPAX ® 4030 EE (EE) | Epax Norway AS | — | 2022000414 |
| Coumarin 6 | Aldrich | — | MKBJ5465V |
| Sodium chloride | Sigma-Aldrich | >99.5% | SZBF3300V |
| Sodium dihydrogen phosphate | Sigma-Aldrich | >99.0% | SLBP1516V |
| Sodium hydroxide | Sigma-Aldrich | >98.0% | SZBBF3240V |
| Instant SIF powder | Biorelevant.com | — | FFF-0519-C |

TABLE 3

Superba Boost ® Specification

| Parameter | Method | Actual Value | Unit |
|---|---|---|---|
| Appearance | Visual | Red viscous oil | |
| Identification | GC-FAME | Conforms | |
| TMA + TMAO | Conway | <2 | mgN/100 g |
| Salts | IPC/IC | 0.1 | g/100 g |
| Total phospholipids | 31P NMR | 58 | g/100 g |
| Phosphatidylcholine | 31P NMR | 52 | g/100 g |
| Choline | 31P NMR | 7 | g/100 g |
| Total Omega-3 fatty acids | AKBM-AM-02 | 31 | g/100 g |
| EPA | AKBM-AM-02 | 16 | g/100 g |
| DHA | AKBM-AM-02 | 9 | g/100 g |
| Peroxide value | AOCS Cd 8b-90 | 3 | g/100 g |
| Astaxanthin | FCC/USP-NF (UV) | 200 | μg/g |
| Astaxanthin esterification (ID) | LC | Conforms | |
| Water activity at 25 C. | Moisture probe | 0.2 | |
| Ethanol | GC | 2 | g/100 g |

Methods

Emulsification

Pure krill oil (KO), fish oil triglyceride (TG), fish oil ethyl ester (EE) and mixtures hereof (KO-TG and KO-EE) were prepared in different ratios. To simulate a realistic scenario where 1-2 ml of KO/FO is ingested with a glass of water, 1% O/W emulsions were prepared using fasted state simulated intestinal fluid (FaSSIF, Table 4) as the aqueous medium. The emulsions were prepared in batches of 10 ml by mixing/dispersing for 1 min using an Ultra-Turrax® T25 disperser from IKA (Staufen im Breisgau, Germany).

TABLE 4

Composition of FaSSIF:

| Compound | Concentration (mM) |
|---|---|
| NaCl | 105.84 |
| NaOH | 10.50 |
| $NaH_2PO_4$ | 28.66 |
| Lecithin | 0.75 |
| Taurocholate | 3.00 |

Emulsion Droplet Size

Emulsions of different compositions of KO, TG, EE and mixtures hereof (Table 5) in FaSSIF were prepared as described above (Table 4). The droplet size of the resulting emulsions was then determined through dynamic light scattering (DLS) using a Zetasizer Nano ZS from Malvern Panalytical (Malvern, UK). The experimental design used to characterize the influence of the different oils on the emulsion droplet size was a full cubic simplex centroid with three center points (18+3) design generated in MODDE® (v. 13.02) from Sartorius (Göttingen, Germany). The data was fitted using a partial least squares (PLS) regression model using both individual and squared (interaction) terms.

TABLE 5

Z-average mean emulsion droplet size determinations from DLS (n = 3):

| | Exp. | | | | | | | | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 |
| KO % | 100 | — | — | 50 | 50 | — | 66.7 | 33.3 | 66.7 | 33.3 | — | — | 33.3 | 66.7 | 16.7 | 16.7 | 33.3 | 33.3 |
| TG % | — | 100 | — | 50 | — | 50 | 33.3 | 66.7 | — | — | 66.7 | 33.3 | 33.3 | 16.7 | 66.7 | 16.7 | 33.3 | 33.3 |
| EE % | — | — | 100 | — | 50 | 50 | — | — | 33.3 | 66.7 | 33.3 | 66.7 | 33.3 | 16.7 | 16.7 | 66.7 | 33.3 | 33.3 |
| Size (nm) | 291 | 1124 | 1701 | 460 | 345 | 1689 | 342 | 487 | 334 | 382 | 1210 | 1646 | 563 | 332 | 505 | 669 | 368 | 372 |

Emulsion Stability

Emulsions of KO, TG, EE, KO-TG (71.4-28.6% w/w) and KO-EE (71.4-28.6% w/w) in FaSSIF were prepared as described above. To better visualize the oil phase of the formulations containing FO (transparent), 0.1% w/w coumarin 6 was dissolved in all formulations prior to emulsification. Immediately after preparation, the five different emulsions were placed in a photo chamber under artificial light. A digital HERO3+ camera from GoPro (San Mateo, CA, USA) was used to record images every 60 sec for 72 h using the time-lapse setting.

Emulsion Droplet Morphology

Emulsions of KO, TG, EE, KO-TG (71.4-28.6% w/w) and KO-EE (71.4-28.6% w/w) in FaSSIF were prepared as described above. Samples for cryogenic transmission electron microscopy (Cryo-TEM) were prepared by depositing 3 μL of the samples on glow-discharged 300 mesh lacey carbon grids from Ted Pella Inc. (Redding, CA, USA). Sample vitrification was then carried out in liquid ethane using a Vitrobot Mark IV from FEI (Hillsboro, OR, USA) under controlled (4° C., 100% relative humidity) and automated blotting conditions. The vitrified samples were then kept in liquid nitrogen and images obtained with an accelerating voltage of 200 kV using a Tecnai G2 20 TWIN Transmission Electron Microscope equipped with a 4K CCD Eagle digital camera from FEI.

Results and Discussion

Emulsion Droplet Size

The size (Z-average mean) of the resulting emulsion droplets after emulsification of the 18 different oil mixtures can be found in Table 5. The mean sizes ranged between 291 nm for pure KO to 1701 nm for pure EE. From Table 5 it is evident that mixing KO in exceeding amounts to compositions with EE and TG lower the droplet size of both EE- and TG-compositions.

Figure 1B:
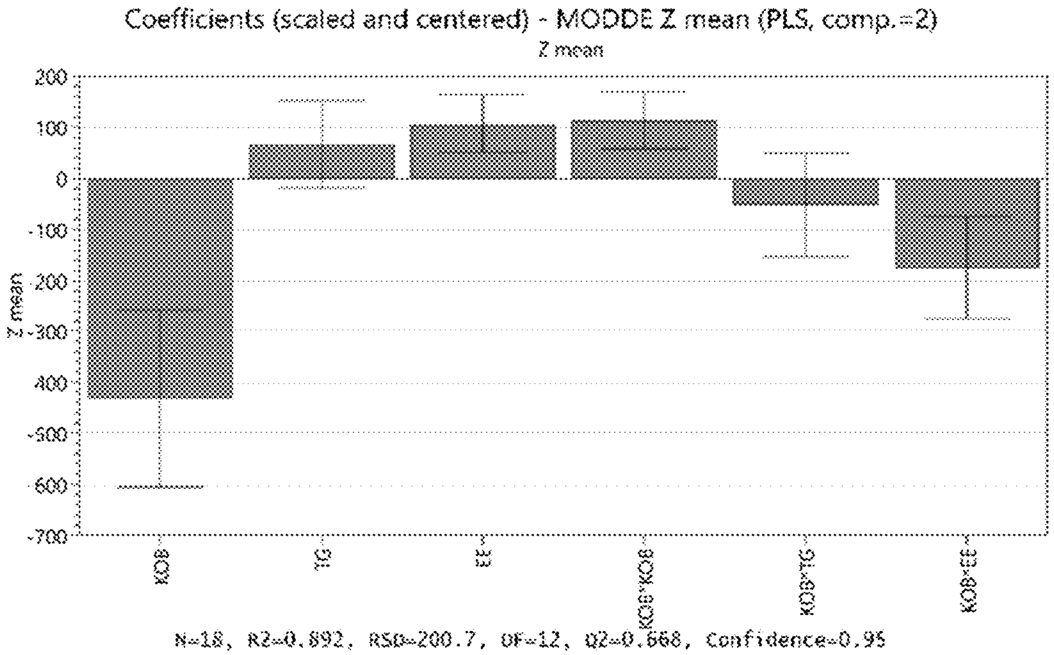
Figure 1C:
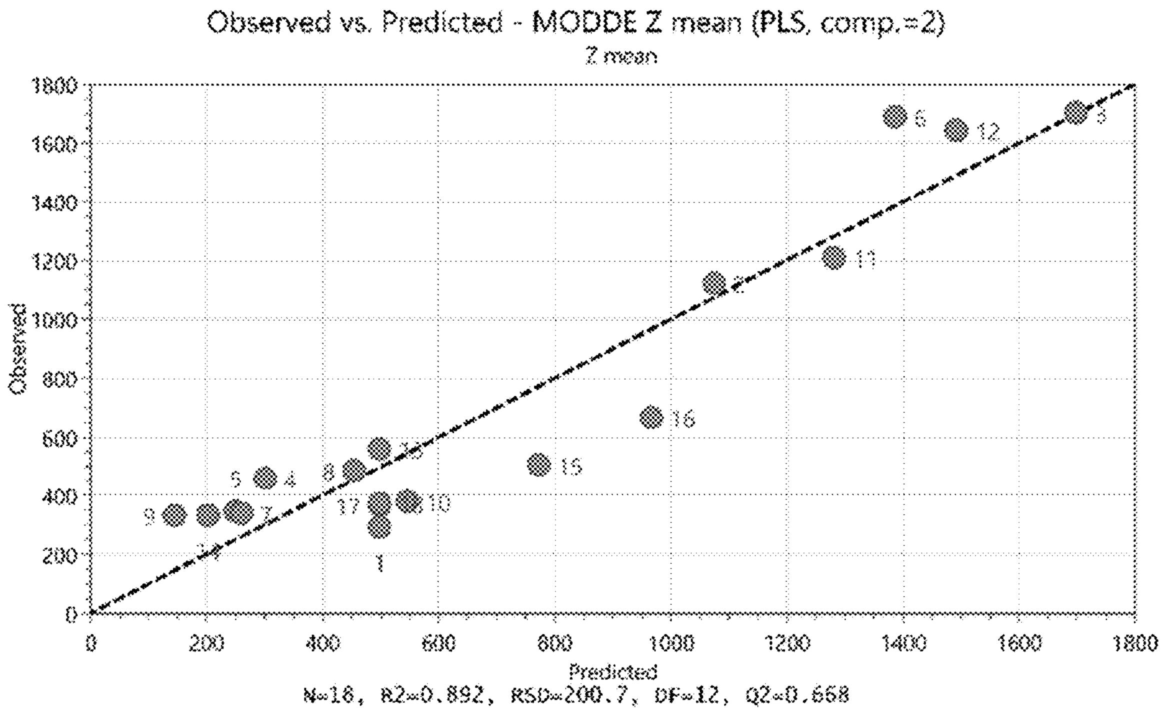

From the Summary of Fit plot (FIG. 1A) it is evident that the resulting PLS model based on the DLS data is accurate, predictive and reproducible (R2>0.80 and other values >0.60). The Coefficients plot of the PLS model (FIG. 1B) support that KO generally have a reducing effect on the mean droplet size in combination products whereas TG and EE generally have an increasing effect on mean droplet size.

Figure 1D:
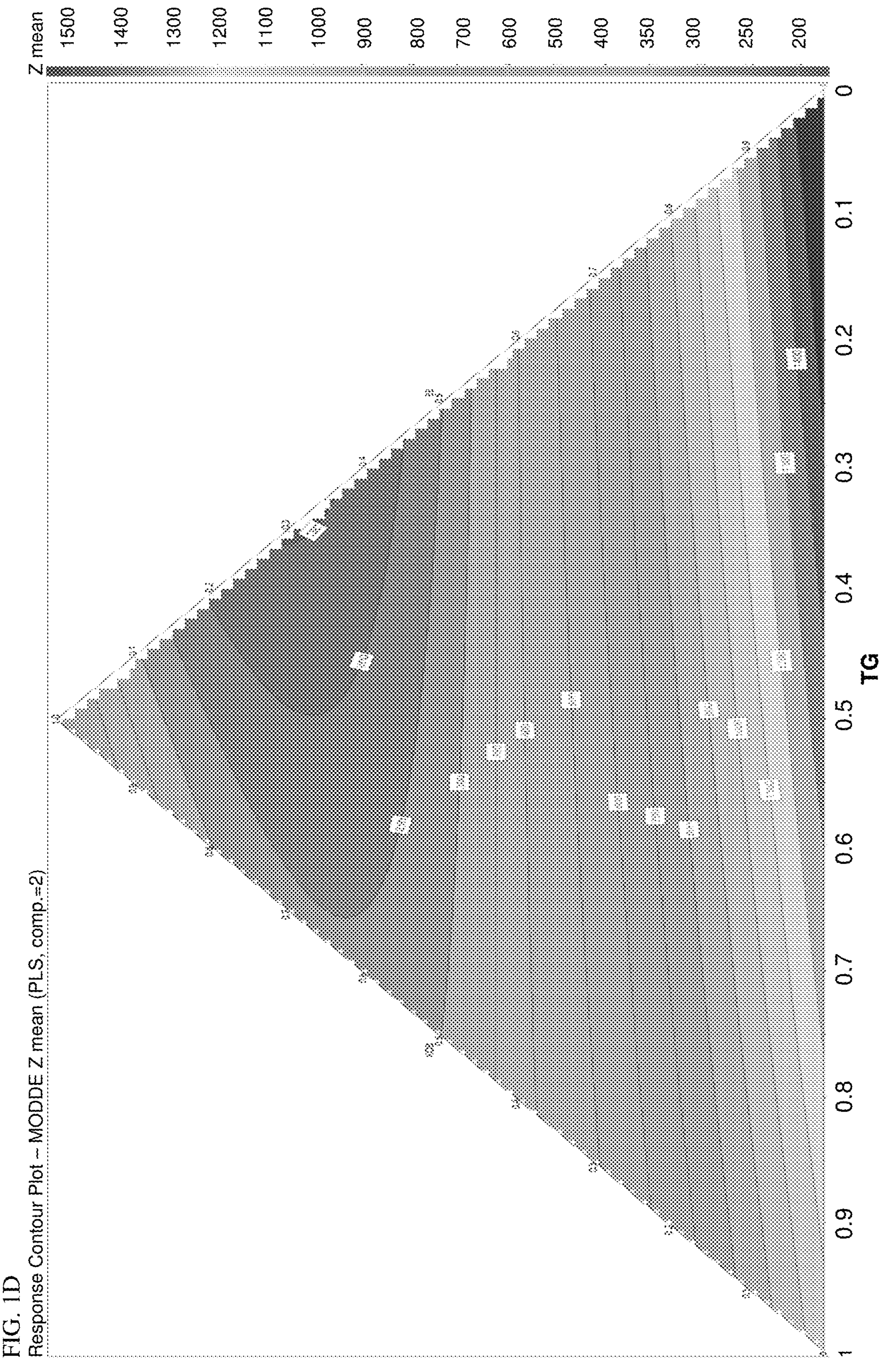

As can be seen from the Table 5 it is not possible to obtain a droplet size below 1000 nm without addition of KO, and below 500 is only obtainable with at least ⅓ KO. The Response Contour Plot in FIG. 1D, which is a visualization of the PLS model derived from the dataset in Table 5, indicate that emulsion droplet sizes below 400 nm can only be achieved in combination compositions that comprises KO concentrations above 40%. The KO used in the experiment is a batch of Superba Boost (batch A102145) with a total PL content of 58% w/w. Accordingly, the PLS model indicate that emulsion droplets below 400 nm are achievable with combination compositions comprising PL of at least 23.2% w/w. Similarly, the model predicts in accordance with the observed data that 30% of KO, corresponding to 17.4% PL, is necessary to achieve emulsion droplets below 500 nm. Furthermore, as indicated by the PLS model, the lowest droplet size is achievable at a KO-EE mixture of around 70:30. This will correspond to lipid formulations comprising 39.2% w/w of the PL and 30% w/w of added EE-EPA and/or EE-DHA.

The emulsion droplet size and surface area to volume of the pure oils and 50:50 mixtures are shown in Table 6. As can be seen, the mixture of KO-EE has a 3.7-5.8 fold larger surface area to volume compared to pure EE and the mixture of KO-TG has a 2.4-3.9 fold larger compared to pure TG. At 70-30 mixtures (corresponding to about 40% w/w of PL from krill and 30% w/w of additional FO-TG or FO-EE) this difference is even more pronounced. This is a significant observation as the bioavailability of lipids may be increased when the droplet size is decreased. This is due to a number of different reasons: 1) smaller droplets have a larger surface area to volume ratio (i.e. larger overall surface area for the same volume) and may therefore be digested faster by digestive enzymes, which release free fatty acids readily available for absorption, 2) smaller droplets may penetrate into the mucous layer of the epithelium cells in the small intestine, thereby increasing their residence time and proximity to the site of absorption, 3) smaller droplets lead to an increase in the aqueous solubility of lipophilic compounds, which may enhance absorption. This demonstrates that when PL from KO is added to FO in both EE and TG form, the resulting emulsion droplets will be smaller with a >4 fold higher surface area, which will lead to faster and more extensive digestion of omega-3 forms into free fatty acids readily available for absorption.

TABLE 6

Surface area to volume calculations for different oil compositions.

| | Diameter (nm) | Radius (nm) | Volume ($nm^3$) | Surface ($nm^2$) | Surface area/mL oil ($m^2$) |
|---|---|---|---|---|---|
| TG | 1124.43 | 562.22 | 744382055 | 3972050 | 5.34 |
| EE | 1701.67 | 850.84 | 2580029369 | 9097049 | 3.53 |
| TG-EE 50:50 | 1688.67 | 844.34 | 2521349130 | 8958586 | 3.55 |
| KO | 291.13 | 145.57 | 12919910 | 266271 | 20.61 |
| KO-TG | 459.733 | 229.87 | 50876316 | 663990 | 13.05 |

TABLE 6-continued

Surface area to volume calculations for different oil compositions.

| | Diameter (nm) | Radius (nm) | Volume ($nm^3$) | Surface ($nm^2$) | Surface area/mL oil ($m^2$) |
|---|---|---|---|---|---|
| 50:50 KO-EE 50:50 | 344.83 | 172.42 | 21469656 | 373566 | 17.40 |

Emulsion Stability

Figure 2:
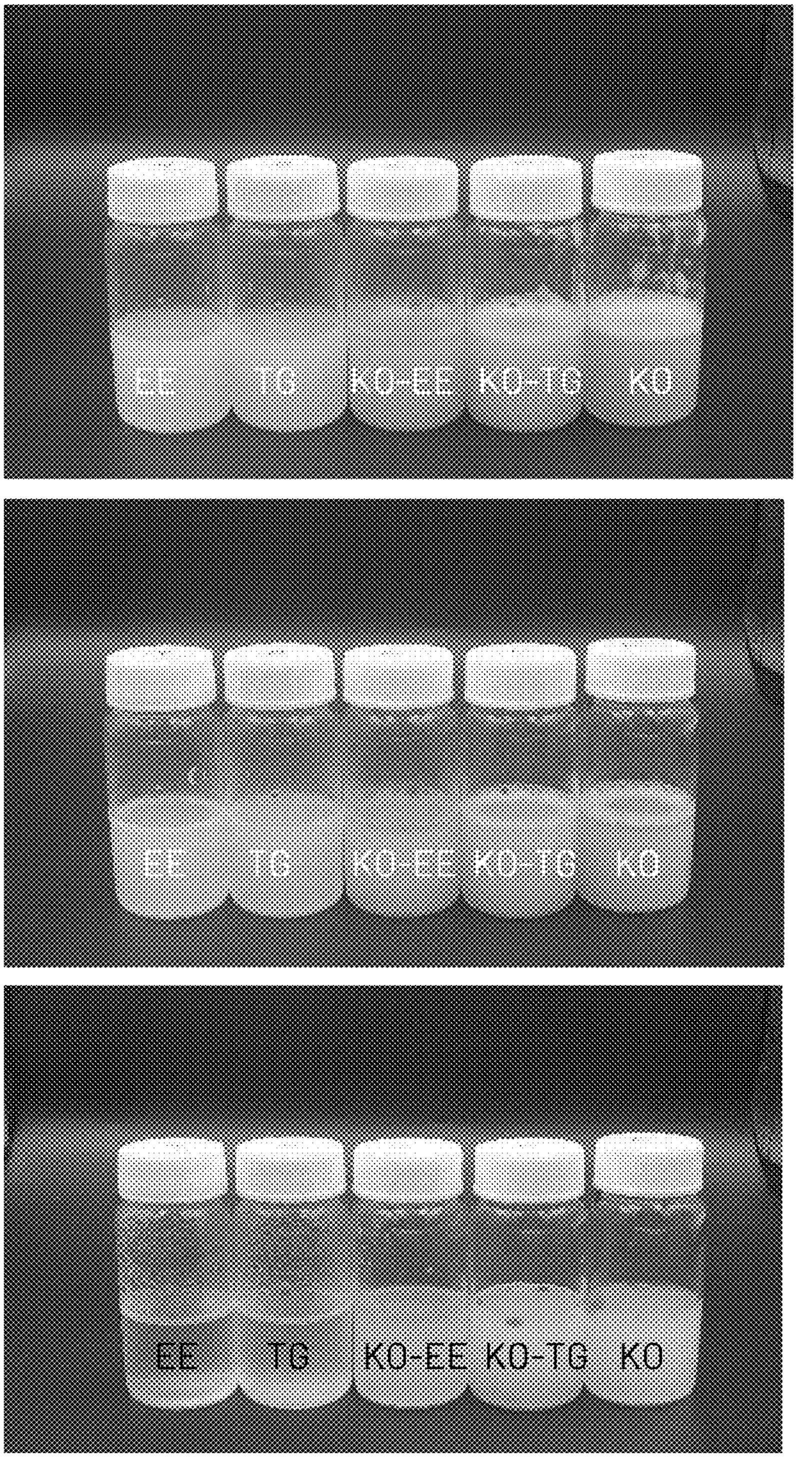
FIG. 2. Images of the freshly prepared emulsion of (from left) EE, TG, KO-EE, KO-TG and KO. Images represent different timepoints after dispersion t=0 min (top), t=20 min (middle) and 48 h (bottom).

Images of the emulsions over time are shown in FIG. 2. As can be seen, the emulsions with pure EE and TG from FOs (1-2) quickly phase separate within minutes-hours as evident from the appearing clear yellow ring on top of the emulsion. The emulsion containing pure KO (5) remains emulsified and cloudy, but does seem to phase separate somewhat over time, although not to the same degree. The phase observed for the KO mixtures (3-4) does not seem oily, which suggests that these phases may consist of astaxanthin and/or neutral lipids from the krill extract with the phospholipids remaining dispersed. This is likely the reason for the lack of fishy aftertaste of mixtures containing KO, contrary to fish oil. By observing the actual emulsion (dispersed) phase over hours-days it is also evident that the two emulsions containing pure fish oils (1-2) become transparent/less opaque faster than the emulsions containing krill oil (3-5). Furthermore, after 72 hours it is evident from the opaqueness of the different emulsions that it seems that the most stable emulsion is formed from the KO-TG mixture (4). This is all in accordance with the findings of the emulsion droplet size study and indicate that mixtures of KO and FOs is likely to perform better than FO alone.

Emulsion Droplet Morphology

Figure 3:
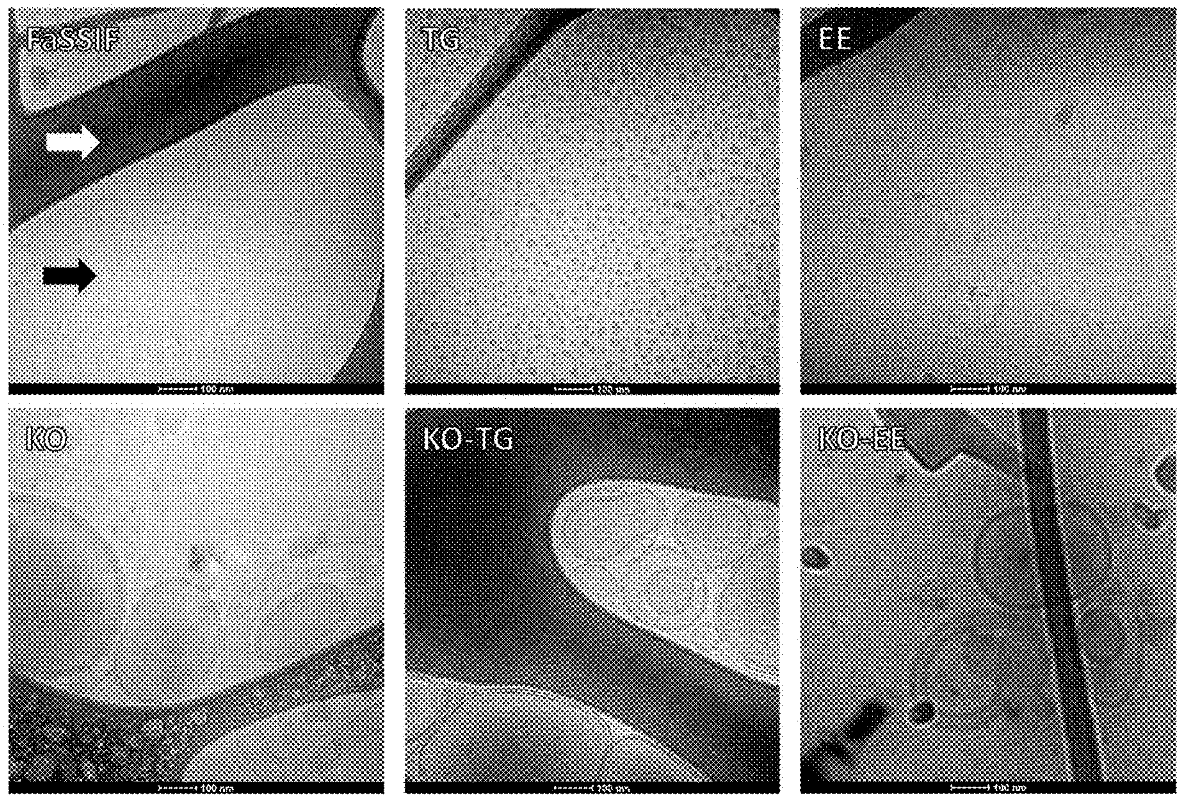
FIG. 3. Cryo-TEM images of the six samples TG, EE, KO, KO-TG (71.4-28.6% w/w) and KO-EE (71.4-28.6% w/w) and FaSSIF alone. The image of KO-EE is of lower resolution compared to the others as it is a zoom of a less magnified image. The carbon grid is marked with a white arrow while the sample area is marked with a black arrow on the FaSSIF micrograph.

The droplet morphology of the six samples (KO, TG, EE, KO-TG 71.4:28.6, KO-EE 71.4:28.6 and FaSSIF) can be seen in FIG. 3. Structures of about 10 nm and smaller are seen in the FaSSIF due to the presence of phospholipids and bile salts. In the TG sample, the process of coalescence has been captured as oil droplets of 20-50 nm can be seen merging to form larger droplets. Had the TG sample been vitrified at a later stage of coalescence, such droplets would likely not have been observed, as the resulting size of the oil droplets would likely be blotted away from the carbon grid during sample preparation. Another potential reason for the absence of larger oil droplets in the micrograph, in the case of the EE sample, could be that inadequate lipid was added to the carbon grid as a result of relatively rapid oil-water phase separation. This is likely the reason that the EE sample appears similar to that of pure FaSSIF. On the other hand, the KO, KO-TG and KO-EE samples all showed several uni- and multilamellar vesicles of sizes ranging from about 100-600 nm. These structures appear more well defined and separated from neighboring vesicles compared to the behavior of the oil droplets from the TG sample. The KO-containing samples would thus likely form more stable systems than the samples without KO.

Conclusion

This study sought to evaluate the emulsifying properties of phospholipids from KO, ethyl esters and triglycerides from FOs and mixtures hereof in relation to gastrointestinal digestibility and absorption/performance. Based on the findings of this study, the lack of fishy aftertaste from mixtures containing PL from KO seems to be related to formation of more stable emulsions upon ingestion i.e. no immediate oil pool formation on top of the stomach content. Furthermore, the mixtures containing PL from KO also displayed an overall lower emulsion droplet size with a surface area 2.4-5.8× higher than that from pure EE and TG from FO, which allows for more rapid digestion into free fatty acids readily available for absorption. Consequently, even though the FOs contain more omega-3 fatty acids than KO it suffers from poor emulsification properties, which limits their digestion and in turn absorption and therefore the overall performance of mixtures with KO may be improved despite the lower overall omega-3 fatty acid content. Finally, from the PLS regression model it can be seen that the optimal ratio for achieving lowest emulsion particles (i.e. highest surface area) is in mixtures with around 70% w/w KO, corresponding to about 40% w/w of phospholipids from krill.

Example 2

The purpose of the study was to investigate transepithelial transport of curcuminoids through an intestinal epithelial cell monolayer, using the Caco-2 cell model. For assessment of the transport of curcuminoids across the Caco-2 monolayer, the cells were seeded on filter membrane inserts and differentiated over 14-21 days for full performance.

In vivo bioavailability of curcuminoids out of curcumin extract is low after oral ingestion due to the poor water solubility. The three main curcuminoids contained in extracts are curcumin (CC), desmethoxycurcumin (DMCC) and bisdesmethoxycurcumin (BDMCC). Within intestinal cells, curcumin can be metabolized to tetrahydrocurcumin (THCC). In the present project, we investigated whether the combination of krill oil and curcumin extract enhance the transport of curcuminoids across the Caco-2 monolayer in vitro.

Test Products:

1. Curcumin, dry powder (Dr. Hittlich)—400 mg CC
2. Krill oil+Curcumin Gelatin Licaps (Greenpower)—200 mg CC
3. Krill oil (Superba Boost)+Curcumin, dry powder (Dr. Hittlich, 2 wt %)—solubilized—40 mg CC Product 3, the solubilized test product, was made by mixing curcumin (2 wt %) with krill oil and EtOH (25 wt %). At end of mixing, the EtOH was evaporated off.

The transepithelial transport of the curcuminoids was assessed after being digested in vitro using an artificial digestion model. The in vitro "artificial digestion" simulates the enzymatic and pH conditions during the gastro-intestinal-passage. At the beginning of this process, one capsule of each test product was added to 105 ml gastric solution. The capsules dissolved within minutes in the gastric solution and resulted in deep orange solutions after 2 h incubation at 37° C. After 4 h at 37° C. under intestinal conditions, all solutions were relatively homogenous.

Differentiated Caco-2 models were supplemented with 10% and 2% of the respective digestion solution for 24 hours. Curcuminoid concentration was determined in the apical compartment at the beginning and in the basolateral compartment after 24 h incubation. Caco-2 monolayers' integrity was monitored before and after the supplementation period by TEER measurement.

The following curcuminoids were determined in the apical supplementation medium samples at the beginning of the supplementation period and the basolateral medium samples at the end of 24 h incubation using LC-MS/MS or HPLC technology:

tetrahydrocurcumin (THCC)
curcumin (CC)

desmethoxycurcumin (DMCC)

bisdesmethoxycurcumin (BDMCC)

All samples, i.e. digestion solution and cell culture medium, were mixed with 0.1% formic acid in acetonitrile (1:1 v/v), vortexed and centrifuged. The supernatant was analyzed using GC/MS method.

A total of 13 subjects successfully completed the study. As shown in Table 7 and in FIG. 6, significant changes from baseline were observed in the average CoQ10 levels of the Krill oil+CoQ10 Formulation group at 6 Hours (p-value=0.006) and 8 Hours (p-value=0.022). No significant absorption was observed in the CoQ10 group at any time point.

TABLE 7

Plasma bioavailability of CoQ10

| | Krill oil + CoQ10 Group | | | CoQ10 Group | | | Between groups | | |
|---|---|---|---|---|---|---|---|---|---|
| | CoQ10 (mg/dL) | Change (%) | p-value | CoQ10 (mg/dL) | Change (%) | p-value | % change difference | % change ratio | p-value |
| Baseline | 0.885 | — | — | 0.992 | — | — | | na | |
| 2 hours | 0.895 | 1.13% | 0.774 | 0.878 | −11.49% | 0.065 | 12.62% | na | 0.047** |
| 4 hours | 1.021 | 15.37% | 0.065 | 0.957 | −4.53% | 0.563 | 19.90% | 3.4 | 0.581 |
| 6 hours | 1.258 | 42.15% | 0.006** | 1.009 | 1.71% | 0.795 | 40.44% | 24.6 | 0.092* |
| 8 hours | 1.095 | 24.73% | 0.022* | 1.053 | 6.15% | 0.468 | 18.58% | 4.0 | 0.063* |

*Significant at alpha = 0.10
**Significant at alpha = 0.05
***Significant at alpha = 0.01
na = not applicable The results demonstrating uptake of curcumin (CC) and the metabolized tetrahydrocurcumin (THCC) in Caco-2 cells can be found in FIG. 6.

Conclusion:

When dry curcumin powder is compared with simple-blended 60% krill oil and 40% curcumin mixture, the transepithelial transport of curcumin was greatly increased as shown in FIG. 5. The absorption characteristics of curcumin can be even more improved in combination with krill PLs with processing techniques to improve the solubility of curcumin further. The improvement in trans-epithelial permeability of curcumin using krill PL is beyond comparison to the dry curcumin powder absorption, possibly also allowing for a formulation that is lower in curcumin concentration while achieving greater health benefits

Example 3

A mixture of phospholipids from krill and curcumin is formulated to have a total phospholipid (PL) content of 40% w/w and a curcumin content of 16.7% w/w. The mixture is encapsulated in 600 mg capsules that provide 240 mg total PL and 100 mg curcumin per capsule.

Example 4

The purpose of the study was to investigate compare the CoQ10 level of absorption in the plasma of a phospholipid krill oil+CoQ10 product to a comparator CoQ10-product (without any krill oil).

Krill oil+CoQ10 Formulation:

Krill oil 500 mg

CoQ10 50 mg

The krill oil used in this study was NKO® with a total PL content of >45% w/w.

CoQ10 Product:

CoQ10 50 mg

Absorption levels of CoQ10 in plasma were measured at time (T)=0, 2, 4, 6 and 8 hours after the single-dose (2 soft gels) intake of the study products. A 7-day minimum wash-out period between the two doses was specified.

A significant between group difference occurred at 2 Hours (p-value=0.047), 6 Hours (p-value=0.092) and 8 Hours (p-value=0.063). Maximal absorption difference of 24.6-fold was obtained at 6 hours. Between-group significance testing at 4 h and 6 h was done using non-parametric test (data non-normally distributed) which explains the p-value decrease in significance at 4 and 6 hours.

Example 5

The example examines whether the emulsifying property of phospholipids from krill oil enhance the uptake of EPA and DHA by comparing pharmacokinetic parameters of two different omega-3 formulations (PL+EPA-DHA vs Ethyl Ester EPA-DHA) in a randomized clinical trial. The main objective was to describe plasma kinetics (AUC; $\Delta C_{max}$, $T_{max}$) of two different omega-3-fatty acids formulations after a single dose. The study was performed as a randomized, two-way cross over pharmacokinetic study with 12 subjects.

Test Products:

Test product, dose, and mode of administration: PL+EPA-DHA, a combination of krill oil phospholipids and fish oil ethyl esters giving a total of 1250 mg EPA & DHA, single oral dose.

Test product, dose, and mode of administration: Fish oil ethyl esters giving a total of 1200 mg EPA & DHA, single oral dose Duration of Intervention:

2 kinetic days, observing plasma levels for 14 hours after single dose plus 24 h, 48 h and 72 h after; 2 weeks of wash-out between the cross-over phases.

Criteria for Evaluation

Primary Objective:

Determination of $iAUC_{0-12h}$ from blood concentration-time curves of EPA+DHA (in plasma) and comparison of $iAUC_{0-12h}$ of EPA+DHA between the study products.

Secondary Objectives:

Determination of $iAUC_{0-72h}$, $iAUC_{0-24h}$, $iAUC_{0-12h}$ (for EPA and DHA), $\Delta C_{max}$ and $T_{max}$ from blood concentration-time curves of EPA, DHA and EPA+DHA (in plasma) and comparison of $iAUC_{0\text{-}72h}$, $iAUC_{0\text{-}24h}$, $iAUC_{0\text{-}12h}$, delta $C_{max}$ and $T_{max}$ between the study products.

p=0.0001) for EPA+DHA (Table 8). Similarly, when EPA and DHA were examined individually, significant differences on iAUCs were found for all three periods.

TABLE 8

Least Square Means from linear mixed model with log-transformed data and treatment ratio between products for iAUC of EPA + DHA over 12, 24 and 72 hours.

| EPA + DHA | EE | | | $PL_+$ | | | Treatment Ratio | | | |
|---|---|---|---|---|---|---|---|---|---|---|
| | | 95% CI | | | 95% CI | | | 95% CI | | |
| Variable | LS Mean | Lower | Upper | LS Mean | Lower | Upper | Ratio | Lower | Upper | p-value |
| $iAUC_{0\text{-}12\ h}$ | 23.2 | 14.9 | 36.0 | 243.4 | 156.4 | 378.9 | 10.51 | 6.11 | 18.08 | <.0001 |
| $iAUC_{0\text{-}24\ h}$ | 37.5 | 22.3 | 63.3 | 467.4 | 277.1 | 788.4 | 12.45 | 5.87 | 26.39 | <.0001 |
| $iAUC_{0\text{-}72\ h}$ | 85.4 | 40.7 | 178.8 | 960.7 | 458.6 | 2012.8 | 11.26 | 3.95 | 32.03 | 0.0001 |

Fatty acid profile at single time points (only descriptively).

Comparison of $iAUC_{0\text{-}72h}$, $iAUC_{0\text{-}24h}$, $iAUC_{0\text{-}12h}$ (for EPA+DHA, EPA and DHA) between study products after dose-adjustment.

Safety Outcomes:

Tolerability.

Safety blood routine parameters.

Adverse events and concomitant medication.

Statistical Methods:

All data obtained in this study and documented in the eCRFs were listed and summarized with descriptive statistics or frequency tables. From concentration-time curves, pharmacokinetic endpoints were calculated for EPA+DHA, EPA and DHA.

Pharmacokinetic endpoints iAUC and $\Delta C_{max}$ were analysed based on log-transformed data using a linear mixed model taking into account sequence (2 levels), period (2 levels), product (2 levels) and baseline omega-3 fatty acid within study period as fixed effects and subject as random effect.

$T_{max}$ were evaluated with non-transformed data using the cross-over analysis by strict separation of treatment effects from period effects. This was achieved via computing the treatment effects separately in two sequence groups formed via randomization. The difference between treatment effects were assessed by means of Wilcoxon rank sum test for independent samples using the intra-individual differences between the outcomes in both periods as the raw data.

All statistical tests were performed two-sided. A p-value less than 5% was considered as statistically significant.

Results & Conclusions

Efficacy Outcomes:

The evaluation of the concentration-time curves demonstrated significantly higher plasma concentrations after intake of PL+EPA-DHA in comparison to the EE EPA-DHA product. This could be shown for the combination of EPA+DHA, and for EPA, and DHA isolated. From concentration-time curves, pharmacokinetic endpoints iAUC, $\Delta C_{max}$ and $T_{max}$ for three different time frames (0-12 h, 0-24 h, 0-72 h) were calculated.

Figure 8:
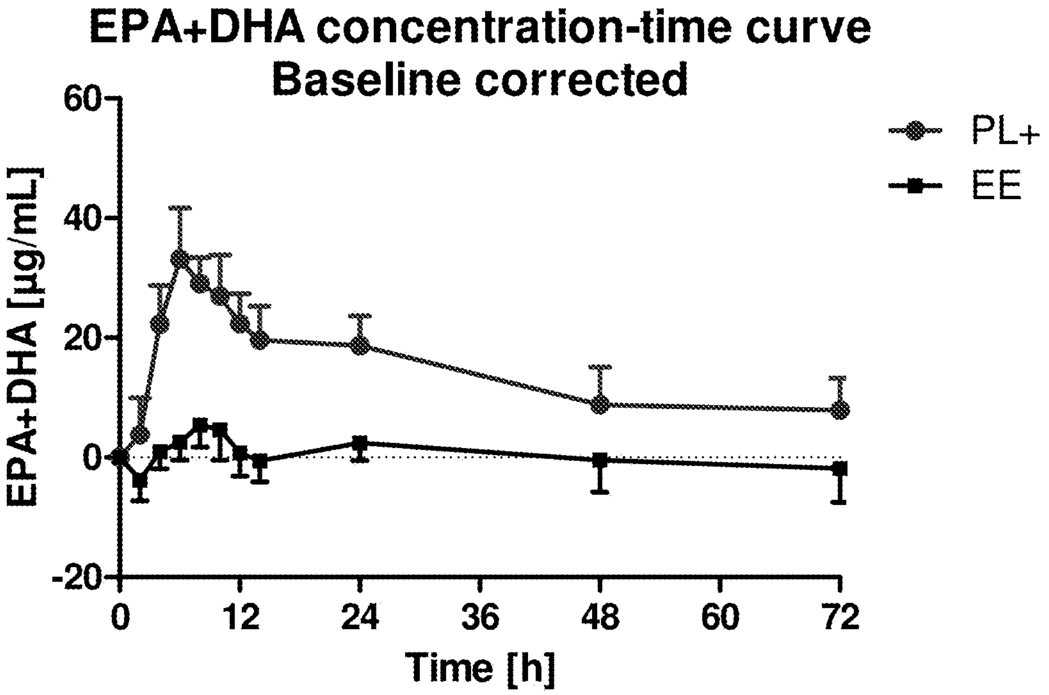
FIG. 8. Graph showing the baseline-corrected time concentration curve of EPA and DHA levels in plasma over 72 hours after ingestion of PL+ EPA-DHA vs EE EPA-DHA product.

The primary endpoint iAUC0-12 h for EPA+DHA was significantly increased after intake of PL+ after baseline adjustment (10.5-fold; p<0.0001; FIG. 8).

The significant difference was also confirmed by iAUC0-24 h (12.4-fold; p<0.0001) and AUC0-72 h (11.2-fold;

Regarding the maximum increase of plasma concentration ($\Delta C_{max}$), significantly higher mean levels were observed for all evaluated parameters (EPA+DHA, EPA, DHA) after intake of PL+EPA-DHA formulation in comparison to the EE product for all three periods.

Time to reach $C_{max}$ values ($T_{max}$) were also evaluated. $T_{max}$ values were quite homogeneously distributed between 6 and 10 hours for EPA+DHA after intake of the PL+EPA-DHA product with a median value of 6 h. In contrast, $T_{max}$ values after intake of the EE product was higher (between 8-11 h), indicating longer period needed to reach peak concentration for EE EPA-DHA product comparing to PL+EPA-DHA product.

Safety Outcomes:

Overall tolerability was very good. Fourteen hours after product intake, 10 out of 12 subjects rated the tolerability as "well tolerated" for the PL+EPA-DHA product and 11 out of 12 for the EE product. During the kinetic days until the 14 h time point no adverse events occurred. One subject reported abdominal pain in the evening after the kinetic day until the next day.

Blood routine parameters were determined at all kinetic days at the 2 h time point and after 72 h. There were no changes that might indicate a relation with administration of the interventional products. The results of this study did not raise any safety concerns.

Conclusions:

Results from this study indicate a significantly 10.5-fold higher uptake of EPA+DHA after intake of the PL+EPA-DHA product in comparison to the EE EPA-DHA product at 12 hours. This could also be confirmed by pharmacokinetic parameters iAUC at 24 hours (12.4-fold) and 72 hours (11.2-fold). In addition, maximum peak concentrations were reached on average slightly faster after the PL+EPA-DHA product in comparison to the EE product. The results clearly confirm that the uptake of fish oil ethyl esters is limited even when consumed with a low-fat meal and this could significantly be improved when providing in a blend with phospholipids as applied in the PL+EPA-DHA product.

Example 6

A mixture of phospholipids from krill and Coenzyme CoQ10 is formulated to have a total phospholipid (PL) content of 40% w/w and a curcumin content of 16.7% w/w. The mixture is encapsulated in 600 mg capsules that provide 240 mg total PL and 100 mg Coenzyme CoQ10 per capsule.

Example 7

A mixture of phospholipids from krill and CBD is formulated to have a total phospholipid (PL) content of 40% w/w and a CBD content of 5% w/w. The mixture is encapsulated in 500 mg capsules that provide 200 mg total PL and 25 mg CBD per capsule.

Example 8

A mixture of phospholipids from krill and ethyl esters and EPA and DHA is formulated to have a total phospholipid (PL) content of 40% w/w and a total DHA/EPA content of 40% w/w. The mixture is encapsulated in 600 mg capsules that provide 240 mg total PL and 250 mg EPA/DHA per capsule.

Example 9

A mixture of phospholipids from krill and a fish oil concentrate comprising EPA and DHA triglycerides is formulated to have a total phospholipid (PL) content of 40% w/w and a total DHA/EPA content of 40% w/w. The mixture is encapsulated in 600 mg capsules that provide 240 mg total PL and 250 mg EPA/DHA per capsule.

Example 10

A mixture of phospholipids from krill and ethyl esters of DHA is formulated to have a total phospholipid (PL) content of 40% w/w and a total DHA content of 31.25% w/w. The mixture is encapsulated in 800 mg capsules that provide 320 mg total PL and 250 mg DHA per capsule.

Example 11

A mixture of phospholipids from krill and a fish oil concentrate comprising DHA triglycerides is formulated to have a total phospholipid (PL) content of 40% w/w and a total DHA content of 31.25% w/w. The mixture is encapsulated in 800 mg capsules that provide 320 mg total PL and 250 mg EPA/DHA per capsule.

REFERENCES

1. Savjani, K. T., A. K. Gajjar, and J. K. Savjani, *Drug solubility: importance and enhancement techniques*. International Scholarly Research Notices, 2012. 2012.
2. Fricker, G., et al., *Phospholipids and lipid-based formulations in oral drug delivery*. Pharmaceutical research, 2010. 27(8): p. 1469-1486.
3. Poovi, G. and N. Damodharan, *Lipid nanoparticles: A challenging approach for oral delivery of BCS Class-II drugs*. Future Journal of Pharmaceutical Sciences, 2018. 4(2): p. 191-205.
4. van Hoogevest, P., *Review-an update on the use of oral phospholipid excipients*. European journal of pharmaceutical sciences, 2017. 108: p. 1-12.
5. Singh, R. P., H. Gangadharappa, and K. Mruthunjaya, *Phospholipids: Unique carriers for drug delivery systems*. Journal of Drug Delivery Science and Technology, 2017. 39: p. 166-179.
6. Li, J., et al., *A review on phospholipids and their main applications in drug delivery systems*. Asian journal of pharmaceutical sciences, 2015. 10(2): p. 81-98.
7. Burri, L., et al., *Marine omega-*3 *phospholipids: metabolism and biological activities*. International journal of molecular sciences, 2012. 13(11): p. 15401-15419.
8. Camera, E., et al., *Astaxanthin, canthaxanthin and β-carotene differently affect UVA-induced oxidative damage and expression of oxidative stress-responsive enzymes*. Experimental dermatology, 2009. 18(3): p. 222-231.
9. Kidd, P., *Astaxanthin, cell membrane nutrient with diverse clinical benefits and anti-aging potential*. Altern Med Rev, 2011. 16(4): p. 355-364.
10. Guerin, M., M. E. Huntley, and M. Olaizola, *Haematococcus astaxanthin: applications for human health and nutrition*. TRENDS in Biotechnology, 2003. 21 (5): p. 210-216.
11. Supplements, N. I.o.H. O.o.D. *Choline—Fact Sheet for Health Professionals*. Jun. 2, 2022 [cited 2022.
12. Jensen, H. H., et al., *Choline in the diets of the US population: NHANES,* 2003-2004. 2007, Wiley Online Library.
13. Sj, S. and L. N. Garth, *The fluid mosaic model of the structure of cell membranes*. Science, 1972. 175(4023): p. 720-731.
14. Killian, J. A. and B. de Kruijff, *Nonbilayer lipids affect peripheral and integral membrane proteins via changes in the lateral pressure profile*. Biochimica et Biophysica Acta (BBA)-Biomembranes, 2004. 1666(1-2): p. 275-288.
15. van der Veen, J. N., et al., *The critical role of phosphatidylcholine and phosphatidylethanolamine metabolism in health and disease*. Biochimica et Biophysica Acta (BBA)-Biomembranes, 2017. 1859(9): p. 1558-1572.
16. Kruijff, B.d., et al., *Lipid polymorphism and membrane function*, in The Enzymes of Biological Membranes. 1985, Springer. p. 131-204.
17. Epand, R. M., *Lipid polymorphism and protein-lipid interactions*. Biochimica et Biophysica Acta (BBA)-Reviews on Biomembranes, 1998. 1376(3): p. 353-368.
18. Siegel, D. and R. Epand, *The mechanism of lamellar-to-inverted hexagonal phase transitions in phosphatidylethanolamine: implications for membrane fusion mechanisms*. Biophysical journal, 1997. 73(6): p. 3089-3111.
19. Thiele, E. A., et al., *Cannabidiol in patients with seizures associated with Lennox-Gastaut syndrome* (*GWP-CARE*4): *a randomised, double-blind, placebo-controlled phase* 3 *trial*. The Lancet, 2018. 391(10125): p. 1085-1096.
20. Devinsky, O., et al., *Trial of cannabidiol for drug-resistant seizures in the Dravet syndrome*. New England Journal of Medicine, 2017. 376(21): p. 2011-2020.
21. Millar, S. A., et al., *Towards better delivery of cannabidiol* (*CBD*). Pharmaceuticals, 2020. 13(9): p. 219.
22. Dependence, W. E. C.o.D., *CANNABIDIOL* (*CBD*) *Pre-Review Report Agenda Item* 5.2. 2017, World Health Organization: Geneva.
23. Silmore, L. H., et al., *Food effects on the formulation, dosing, and administration of cannabidiol* (*CBD*) *in humans: A systematic review of clinical studies*. Pharmacotherapy: The Journal of Human Pharmacology and Drug Therapy, 2021. 41(4): p. 405-420.
24. Hellriegel, E. T., T. D. Bjornsson, and W. W. Hauck, *Interpatient variability in bioavailability is related to the extent of absorption: implications for bioavailability and bioequivalence studies*. Clinical Pharmacology & Therapeutics, 1996. 60(6): p. 601-607.

25. Feeney, O. M., et al., 50 *years of oral lipid-based formulations: provenance, progress and future perspectives*. Advanced Drug Delivery Reviews, 2016. 101: p. 167-194.

26. Hildebrandt, A. L., D. M. Kelly-Sullivan, and S. C. Black, *Antiobesity effects of chronic cannabinoid CB*1 *receptor antagonist treatment in diet-induced obese mice*. European journal of pharmacology, 2003. 462(1-3): p. 125-132.

27. Devane, W. A., et al., *Determination and characterization of a cannabinoid receptor in rat brain*. Molecular pharmacology, 1988. 34(5): p. 605-613.

28. Devane, W. A., et al., *Isolation and structure of a brain constituent that binds to the cannabinoid receptor*. Science, 1992. 258(5090): p. 1946-1949.

29. Komarnytsky, S., et al., *Endocannabinoid system and its regulation by polyunsaturated fatty acids and full spectrum hemp oils*. International Journal of Molecular Sciences, 2021. 22(11): p. 5479.

30. Grant, K. L. and C. D. Schneider, *Alternative therapies*. American Journal of Health-System Pharmacy, 2000. 57(12): p. 1121-1122.

31. Hsu, C.-H. and A.-L. Cheng, *Clinical studies with curcumin*. The molecular targets and therapeutic uses of curcumin in health and disease, 2007: p. 471-480.

32. Sharma, R., A. Gescher, and W. Steward, *Curcumin: the story so far*. European journal of cancer, 2005. 41(13): p. 1955-1968.

33. Liu, W., et al., *Oral bioavailability of curcumin: problems and advancements*. Journal of drug targeting, 2016. 24(8): p. 694-702.

34. Liu, Z., J. D. Smart, and A. S. Pannala, *Recent developments in formulation design for improving oral bioavailability of curcumin: a review*. Journal of drug delivery science and technology, 2020. 60: p. 102082.

35. Velasco-Rodríguez, L.d.C., et al., *Krill lecithin as surfactant for preparation of oil/water nanoemulsions as curcumin carriers*. European Journal of Lipid Science and Technology, 2021. 123(9): p. 2000238.

36. Wu, Y., et al., *Curcumin-loaded liposomes prepared from bovine milk and krill phospholipids: Effects of chemical composition on storage stability, in-vitro digestibility and anti-hyperglycemic properties*. Food Research International, 2020. 136: p. 109301.

37. Ibrahim, S., et al., *Curcumin marinosomes as promising nano-drug delivery system for lung cancer*. International journal of pharmaceutics, 2018. 540(1-2): p. 40-49.

38. Angelis, I. D. and L. Turco, *Caco*-2 *cells as a model for intestinal absorption*. Current protocols in toxicology, 2011. 47(1): p. 20.6. 1-20.6. 15.

39. Crane, F. L., *Biochemical functions of coenzyme Q*10. Journal of the American College of Nutrition, 2001. 20(6): p. 591-598.

40. Bonakdar, R. A. and E. Guarneri, *Coenzyme Q*10. American family physician, 2005. 72(6): p. 1065-1070.

41. Díaz-Casado, M. E., et al., *The paradox of coenzyme Q*10 *in aging*. Nutrients, 2019. 11(9): p. 2221.

42. Hernández-Camacho, J. D., et al., Coenzyme Q10 *supplementation in aging and disease*. Frontiers in physiology, 2018. 9: p. 44.

43. Kommuru, T., et al., *Self-emulsifying drug delivery systems (SEDDS) of coenzyme Q*10: *formulation development and bioavailability assessment*. International journal of pharmaceutics, 2001. 212(2): p. 233-246.

44. Beg, S., S. Javed, and K. JKohli, *Bioavailability enhancement of coenzyme Q*10: *an extensive review of patents*. Recent patents on drug delivery & formulation, 2010. 4(3): p. 245-257.

45. Molyneux, S., et al., *The bioavailability of coenzyme Q*10 *supplements available in New Zealand differs markedly*. The New Zealand Medical Journal (Online), 2004. 117(1203).

46. Banni, S. and V. Di Marzo, *Effect of dietary fat on endocannabinoids and related mediators: consequences on energy homeostasis, inflammation and mood*. Molecular nutrition & food research, 2010. 54(1): p. 82-92.

47. Calder, P. C., *Marine omega*-3 *fatty acids and inflammatory processes: Effects, mechanisms and clinical relevance*. Biochimica et Biophysica Acta (BBA)-Molecular and Cell Biology of Lipids, 2015. 1851(4): p. 469-484.

48. Cottin, S., T. Sanders, and W. Hall, *The differential effects of EPA and DHA on cardiovascular risk factors*. Proceedings of the Nutrition Society, 2011. 70(2): p. 215-231.

49. Dyall, S. and A. Michael-Titus, *Neurological benefits of omega*-3 *fatty acids*. Neuromolecular medicine, 2008. 10(4): p. 219-235.

50. Hibbeln, J. R., et al., *Healthy intakes of n*-3 *and n*-6 *fatty acids: estimations considering worldwide diversity*. The American journal of clinical nutrition, 2006. 83(6): p. 1483S-1493S.

51. Simopoulos, A. P., *The importance of the omega*-6/ *omega*-3 *fatty acid ratio in cardiovascular disease and other chronic diseases*. Experimental biology and medicine, 2008. 233(6): p. 674-688.

52. Dyerberg, J., et al., *Bioavailability of marine n*-3 *fatty acid formulations*. Prostaglandins, Leukotrienes and Essential Fatty Acids, 2010. 83(3): p. 137-141.

53. Berge, K., et al., *Krill oil supplementation lowers serum triglycerides without increasing low-density lipoprotein cholesterol in adults with borderline high or high triglyceride levels*. Nutrition research, 2014. 34(2): p. 126-133.

54. Amate, L., A. Gil, and M.a. Ramirez, *Dietary long-chain polyunsaturated fatty acids from different sources affect fat and fatty acid excretions in rats*. The Journal of nutrition, 2001. 131(12): p. 3216-3221.

55. Bloom, B., et al., *Absorption of phospholipides: manner of transport from intestinal lumen to lacteals*. American Journal of Physiology-Legacy Content, 1954. 177(1): p. 84-86.

56. Dahan, A., et al., *The oral absorption of phospholipid prodrugs: In vivo and in vitro mechanistic investigation of trafficking of a lecithin-valproic acid conjugate following oral administration*. Journal of controlled release, 2008. 126(1): p. 1-9.

57. Nishimukai, M., H. Hara, and Y. Aoyama, *Enteral administration of soyabean lecithin enhanced lymphatic absorption of triacylglycerol in rats*. British Journal of Nutrition, 2003. 90(3): p. 565-571.

58. Ramirez, M., L. Amate, and A. Gil, *Absorption and distribution of dietary fatty acids from different sources*. Early human development, 2001. 65: p. S95-S101.

59. Rodgers, J., R. O'Brien, and J. Balint, *The absorption and subsequent utilization of lecithin by the rat jejunum*. The American Journal of Digestive Diseases, 1975. 20(3): p. 208-213.

60. Song, J.-H., Y. Inoue, and T. Miyazawa, *Oxidative stability of docosahexaenoic acid-containing oils in the form of phospholipids, triacylglycerols, and ethyl esters*. Bioscience, biotechnology, and biochemistry, 1997. 61(12): p. 2085-2088.

61. Tso, P., et al., *Role of biliary phosphatidylcholine in the absorption and transport of dietary triolein in the rat.* Gastroenterology, 1981. 80(1): p. 60-65.

62. Garaiova, I., et al., *A randomised cross-over trial in healthy adults indicating improved absorption of omega-*3 *fatty acids by pre-emulsification*. Nutrition Journal, 2007. 6(1): p. 1-9.

63. Raatz, S. K., et al., *Enhanced absorption of n-*3 *fatty acids from emulsified compared with encapsulated fish oil.* Journal of the American Dietetic Association, 2009. 109(6): p. 1076-1081.

The invention claimed is:

1. A lipid formulation for use in therapy by enhancing absorption of a therapeutic ingredient in a subject in need thereof, comprising:

a) phospholipids from a marine source, wherein the phospholipids comprise more than 80% w/w phosphatidylcholine and wherein the molar content of omega-3 moieties in the phospholipids is more than 25%; and b) a therapeutic ingredient selected from the group consisting of a substance classified as class 2, 3 or 4 according to the Biopharmaceutical classification system (BCS) and a lipophilic substance from a source different from the marine source for the phospholipids;

wherein the lipid formulation comprises more than 17% w/w of phospholipids and forms emulsions selected from the group consisting of emulsions with a droplet size of from 150 nm to 600 nm in an artificial stomach fluid determined through dynamic light scattering.

2. The lipid formulation for use according to claim 1, wherein the lipid formulation comprises from 2.5% to 50% w/w of the therapeutic ingredient.

3. The lipid formulation for use according to claim 1, wherein the lipid formulation comprises from 15% to 50% w/w of the lipophilic substance from a source different from the marine source of the phospholipids.

4. The lipid formulation for use according to claim 1, wherein the substance from a source different than the marine source of the phospholipids is selected from the group consisting of ethyl esters, triglycerides and combinations thereof.

5. The lipid formulation for use according to claim 1, wherein the lipophilic substance from a source different than the marine source of the phospholipids is an algal oil.

6. The lipid formulation for use according to claim 5, wherein the lipid formulation comprises from 20% to 50% w/w of the algal oil.

7. The lipid formulation for use according claim 1, wherein the lipid formulation comprises from 17% to 70% w/w of the phospholipids from the marine source.

8. The lipid formulation for use according claim 1, wherein the lipid formulation comprises from 20% to 60% w/w of the phospholipids from the marine source.

9. The lipid formulation for use according claim 1, wherein the lipid formulation comprises from 30% to 50% w/w of the phospholipids from the marine source.

10. The lipid formulation for use according to claim 1, wherein the lipid formulation forms a droplet size of from 150 to 500 nm in an artificial stomach fluid determined through dynamic light scattering.

11. The lipid formulation for use according to claim 1, wherein the lipid formulation forms a droplet size of from 150 to 250 nm in an artificial stomach fluid determined through dynamic light scattering.

12. The lipid formulation for use according to claim 1, wherein the lipid formulation forms a droplet size of from 150 to 200 nm in an artificial stomach fluid determined through dynamic light scattering.

13. The lipid formulation for use according to claim 1, wherein the lipid formulation forms an emulsion comprising droplets wherein at least 80% of the droplets have a droplet size of from 150 to 500 nm in an artificial stomach fluid.

14. The lipid formulation for use according to claim 1, wherein the lipid formulation forms an emulsion comprising droplets wherein at least 80% of the droplets have a droplet size of from 150 to 300 nm in an artificial stomach fluid determined through dynamic light scattering.

15. The lipid formulation for use according to claim 1, wherein the lipid formulation forms an emulsion comprising droplets wherein at least 80% of the droplets have a droplet size of from 150 to 250 nm in an artificial stomach fluid determined through dynamic light scattering.

16. The lipid formulation for use according to claim 1, wherein the lipid formulation forms an emulsion comprising droplets wherein at least 80% of the droplets have a droplet size of from 150 to 200 nm in an artificial stomach fluid determined through dynamic light scattering.

* * * * *